(12) United States Patent
Abbott et al.

(10) Patent No.: US 6,881,564 B1
(45) Date of Patent: Apr. 19, 2005

(54) DIPEPTIDYL PEPTIDASES

(75) Inventors: Catherine Anne Abbott, Parkside (AU); Mark Douglas Gorrell, Annandale (AU)

(73) Assignee: The University of Sydney, Sydney (AU)

( * ) Notice: Subject to any disclaimer, the term of this patent is extended or adjusted under 35 U.S.C. 154(b) by 163 days.

(21) Appl. No.: 10/070,464

(22) PCT Filed: Sep. 11, 2000

(86) PCT No.: PCT/AU00/01085

§ 371 (c)(1), (2), (4) Date: Jul. 18, 2002

(87) PCT Pub. No.: WO01/19866

PCT Pub. Date: Mar. 22, 2001

(30) Foreign Application Priority Data

Sep. 10, 1999 (AU) .............................. PQ 2762
Feb. 18, 2000 (AU) .............................. PQ 5709

(51) Int. Cl.[7] ................................. C12N 9/64
(52) U.S. Cl. ..................................... 435/226
(58) Field of Search ........................... 435/226

(56) References Cited

U.S. PATENT DOCUMENTS 4,977,085 A * 12/1990 Sprague et al. ............. 435/212

OTHER PUBLICATIONS

Qi et al Human DPPIV related serine protease DPRP–1. from WO200231134 Apr.–18–2002. SeqABG61591. Alignment with SEQ ID No.: 1.*

Kawakami et al EMBL Acc#AK000290 alignment with SEQ ID No.:1 Feb. 22, 2000.*

Database EMBL'Online! retrieved from EMBL Database accession No. AA417787; XP002266787 (Abstract).

Database EMBL'Online! retrieved from EMBL Database accession No. AA278625; XP002266788 (Abstract).

Database EMBL'Online! retrieved from EMBL Database accession No. AA496257; XP002266789 (Abstract).

* cited by examiner

*Primary Examiner*—Rebecca E. Prouty
*Assistant Examiner*—Sheridan L. Swope
(74) *Attorney, Agent, or Firm*—Olson & Hierl, Ltd.

(57) ABSTRACT

The present invention provides an isolated peptide that comprises the sequence shown in SEQ ID NO:1 or a sequence which has at least 95% identity with SEQ ID NO:1, and which has the same substrate specificity as SEQ ID NO:1. Preferred peptides include peptides having the amino acid sequences set forth in SEQ ID NO: 3, 5, and 7. The isolated peptide is useful as a dipeptidyl aminopeptidase.

8 Claims, 9 Drawing Sheets

FIGURE 2 large DPP8 transcript →
mall DPP8 transcript → mouse DPP8

DIPEPTIDYL PEPTIDASES

FIELD OF INVENTION

The invention relates to a dipeptidyl peptidase, to a nucleic acid molecule which encodes it, and to uses of the peptidase.

BACKGROUND OF THE INVENTION

The dipeptidyl peptidase (DPP) IV-like gene family is a family of molecules which have related protein structure and function [1–3]. The gene family includes the following molecules: DPPIV (CD26), dipeptidyl amino-peptidase-like protein (DPP6) and fibroblast activation protein (FAP) [1,2, 4,5]. Another possible member is DPPIV-β [6].

The molecules of the DPPIV-like gene family are serine proteases, they are members of the peptidase family S9b, and together with prolyl endopeptidase (S9a) and acylaminoacyl peptidase (S9c), they are comprised in the prolyl oligopeptidase family[5,7].

DPPIV and FAP both have similar postproline dipeptidyl amino peptidase activity, however, unlike DPPIV, FAP also has gelatinase activityt[8,9].

DPPIV substrates include chemokines such as RANTES, eotaxin, macrophage-derived chemokine and stromal-cell-derived factor 1; growth factors such as glucagon and glucagon-like peptides 1 and 2; neuropeptides including neuropeptide Y and substance P; and vasoactive peptides [10–12].

DPPIV and FAP also have non-catalytic activity; DPPIV binds adenosine deaminase, and FAP binds to $\alpha_3\beta_1$ and $\alpha_5\beta_1$ integrin[13–14].

In view of the above activities, the DPPIV-like family members are likely to have roles in intestinal and renal handling of proline containing peptides, cell adhesion, peptide metabolism, including metabolism of cytokines, neuropeptides, growth factors and chemokines, and immunological processes, specifically T cell stimulation[3,11,12].

Consequently, the DPPIV-like family members are likely to be involved in the pathology of disease, including for example, tumour growth and biology, type II diabetes, cirrhosis, autoimmunity, graft rejection and HIV infection [3,15–18].

Inhibitors of DPPIV have been shown to suppress arthritis, and to prolong cardiac allograft survival in animal models in vivo[9,20]. Some DPPIV inhibitors are reported to inhibit HIV infection[21]. It is anticipated that DPPIV inhibitors will be useful in other therapeutic applications including treating diarrhoea, growth hormone deficiency, lowering glucose levels in non insulin dependent diabetes mellitus and other disorders involving glucose intolerance, enhancing mucosal regeneration and as immunosuppressants[3,21–24].

There is a need to identify members of the DPPIV-like gene family as this will allow the identification of inhibitor (s) with specificity for particular family member(s), which can then be administered for the purpose of treatment of disease. Alternatively, the identified member may of itself be useful for the treatment of disease.

SUMMARY OF THE INVENTION

The present invention seeks to address the above identified need and in a first aspect provides a peptide which comprises the amino acid sequence shown in SEQ ID NO:1. This peptide has substrate specificity for the following compounds: H-Ala-Pro-pNA, H-Gly-Pro-pNA and H-Arg-Pro-pNA. Therefore, it is a prolyl oligopeptidase and a dipeptidyl peptidase, because it is capable of hydrolysing the peptide bond C-terminal to proline in each of these compounds.

The peptide is homologous with human DPPIV, and importantly, identity between the sequences of DPPIV and SEQ ID NO: 1 is observed at the region of DPPIV containing the catalytic triad residues and the two glutamate residues of the β-propeller domain essential for DPPIV enzyme activity. The observation of amino acid sequence homology means that the peptide which has the amino acid sequence shown in SEQ ID NO:1 is a member of the DPPIV-like gene family. Accordingly the peptide was provisionally named DPPIVL1, and is now named and described herein as DPP8.

The following sequences of the human DPPIV amino acid sequence are important for the catalytic activity of DPPIV: (i) $Tyr^{627}GlyTrpSerTyrGlyGlyTyrVal$ (SEQ ID NO: 9); (ii) $Ala^{707}AspAspAsnValHisPhe$ (SEQ ID NO: 10); (iii) $Glu^{738}AspHisGlyIleAlaGln$ (SEQ ID NO: 11): and (iv) $Tyr^{201}ValTyrGluGluGluVal$ (SEQ ID NO: 12) [25–28]. As described herein, the alignment of the following sequences of DPP8: $His^{736}GlyTrpSerTyrGlyGlyTyrLeu$ (SEQ ID NO: 13); $Leu^{816}AspGluAsnValHisPheAla$ (SEQ ID NO: 14); $Glu^{847}ArgHisSerIleArg$ (SEQ ID NO: 15) and $Phe^{255}ValLeuGlnGluGluPhe$ (SEQ ID NO: 16) with sequences (i) to (iv) above, respectively, suggests that these sequences of DPP8 are likely to confer the catalytic activity of DPP8. Thus, in a second aspect, the invention provides a peptide comprising the following amino acid sequences: $His^{736}GlyTrpSerTyrGlyGlyTyrLeu$ (SEQ ID NO: 13); $Leu^{816}AspGluAsnVallIisPheAlaHis$ (SEQ ID NO: 17); $Glu^{847}ArgHisSerIleArg$ (SEQ ID NO: 15) and $Phe^{255}ValLeuGlnGluGluPhe$ (SEQ ID NO: 16); which has the substrate specificity of the sequence shown in SEQ ID NO:1.

Also described herein, using nmultiple sequence alignment, it is observed that DPP8 has 55% amino acid similarity and 32% amino acid identity with a *C. elegans* protein. Further, as shown herein, a nucleic acid molecule which encodes DPP8, is capable of hybridising specifically with DPP8 sequeuces derived from non-human species. Together these data suggest that DPP8 is expressed in non-human species. Thus in a third aspect, the invention provides a peptide which has at least 60% amino acid identity with the amino acid sequence shown in SEQ ID NO: 1, and which has the substrate specificity of the sequence shown in SEQ ID NO: 1. Preferably, the amino acid identity is 75%. More preferably, the amino acid identity is 95%. Amino acid identity is calculated using GAP software [GCG Version 8, Genetics Computer Group, Madison, Wis., USA] as described further herein. Typically, the non-human DPP8 comprises the following sequences: $His^{736}GlyTrpSerTyrGlyGlyTyrLeu$ (SEQ ID NO: 13); $Leu^{816}AspGluAsnValHisPheAlaHis$ (SEQ ID NO: 17); $Glu^{847}ArgHisSerIleArg$ (SEQ ID NO: 15) and $Phe^{255}ValleuGlnGluGluPhe$ (SEQ ID NO i6).

In view of the homology between DPPIV and DPP8 amino acid sequences, it is expected that these sequences will have similar tertiary structure. This means that the tertiary structure of DPP8 is likely to include the seven-blade β-propeller domain and the α/β hydrolasc domain of DPPIV. These structures in DPP8 are likely to be conferred by the regions comprising β-propeller, $Gly^{180}$ to $Asp^{606}$, a/b hydrolase, $Ser^{607}$ to $Ile^{882}$ and about 70 to 100 residues in the region $Arg^{39}$ to $Gln^{179}$. As it is known that the β-propeller domain regulates proteolysis mediated by the catalytic triad in the α/β hydrolase domain of Prolyl oligopeptidase, [29] it is expected that truncated forms of DPP8 can be produced, which have the substrate specificity sequence shown in SEQ ID NO: 1 comprising the regions referred to above (His$^{736}$GlyTrpSerTyrGlyGlyTyrLeu (SEQ ID NO: 13): Leu$^{816}$AspGluAsnValHisPheAlaHis (SEQ ID NO: 17); Glu$^{847}$ArgHisSerIleArg (SEQ ID NO: 15) and Phe$^{255}$ValLeuGlnGluGluPhe (SEQ ID NO: 16)) which confer the catalytic specificity of DPP8. Examples of truncated forms of DPP8 which might be prepared are those in which the region conferring the β-propeller domain and the α/β hydrolase domain are spliced together. Other examples of truncated forms include those which are encoded by splice variants of DPP8 mRNA. Thus although, as described herein, the biochemical characterisation of DPP8 shows that DPP8 consists of 882 amino acids and has a molecular weight of about 100 kDa, it is recognised that truncated forms of DPP8 which have the substrate specificity of the sequence shown in SEQ ID NO: 1, may be prepared using standard techniques [30,31]. Thus in a fourth aspect, the invention provides a fragment of the sequence shown in SEQ ID NO: 1, which has the substrate specificity of the sequence shown in SEQ ID NO: 1. Preferably, the fragment has an amino acid sequence shown in SEQ ID NO: 3, 5 or 7.

As described herein, the sequence shown in SEQ ID NO:1 does not contain a consensus sequence for N-linked glycosylation. Therefore it is unlikely that DPP8 is associated with N-linked glycosylation. In this regard, DPP8 is distinguished from other DPPIV-like gene family members, which contain between 6 and 9 consensus sequences for N-linked glycosylation. Thus in one embodiment, an asparagine residue in the peptide of the first aspect of the invention is not linked to a carbohydrate molecule. The analysis of DPP8 expression described herein shows that it is likely that DPP8 is expressed as a cytoplasmic protein. The expression of DPP8 is therefore distinguished from other DPPIV-like gene family members, which are expressed on the cytoplasmic membrane, or in other words, the cell surface membrane. Thus in another embodiment, the peptide of the first aspect of the invention is not expressed on a cell surface membrane of a cell.

It is recognised that DPP8 may be fused, or in other words, linked to a further amino acid sequence, to form a fusion protein which has the substrate specificity of the sequence shown in SEQ ID NO:1. An example of a fusion protein is described herein which comprises the sequence shown in SEQ ID NO:1 which is linked to a further amino acid sequence: a "tag" sequence which consists of an amino acid sequence encoding the V5 epitope and a His tag. An example of another further amino acid sequence which may be linked with DPP8 is a glutathione S transferase (GST) domain [30]. Another example of a further amino acid sequence is a portion of CD8α [8]. Thus in one aspect, the invention provides a fusion protein comprising the amino acid sequence shown in SEQ ID NO:1 linked with a further amino acid sequence, the fusion protein having the substrate specificity of the sequence shown in SEQ ID NO:1.

It is also recognised that the peptide of the first aspect of the invention may be comprised in a polypeptide, so that the polypeptide has the substrate specificity of DPP8. The polypeptide may be useful, for example, for altering the protease susceptibility of DPP8, when used in in vivo applications. An example of a polypeptide which may be useful in this regard, is albumin. Thus in another embodiment, the peptide of the first aspect is comprised in a polypeptide which has the substrate specificity of DPP8.

As described above, the isolation and characterisation of DPP8 is necessary for identifying inhibitors of DPP8 catalytic activity, which may be useful for the treatment of disease. A method for identifying inhibitors of DPP8 catalytic activity, described herein, has identified that various inhibitors of DPPIV and serine proteases, zinc and mimetic peptides, Ala-Pro-Gly and Lys-Pro, but not inhibitors of metalloproteinases, aspartyl proteinases or cysteinyl proteinases, inhibit DPP8 catalytic activity. Accordingly, in a fifth aspect, the invention provides a method of identifying a molecule capable of inhibiting cleavage of a substrate by DPP8, the method comprising the following steps:

(a) contacting DPP8 with the molecule;

(b) contacting DPP8 of step (a) with a substrate capable of being cleaved by DPP8, in conditions sufficient for cleavage of the substrate by DPP8; and (c) detecting substrate not cleaved by DPP8, to identify that the molecule is capable of inhibiting cleavage of the substrate by DPP8.

It is recognised that although inhibitors of DPP8 may also inhibit DPPIV and other serine proteases, as described herein, the alignment of the DPP8 amino acid sequence with most closely related molecules,(i.e. DPPIV), reveals that the DPP8 amino acid is distinctive, particularly at the regions controlling substrate specificity. Accordingly, it is expected that it will be possible to identify inhibitors which inhibit DPP8 catalytic activity specifically, which do not inhibit catalytic activity of DPPIV-like gene family members, or other serine proteases. Thus, in a sixth aspect, the invention provides a method of identifying a molecule capable of inhibiting specifically, the cleavage of a substrate by DPP8, the method comprising the following steps:

(a) contacting DPP8 and a further protease with the molecule;

(b) contacting DPP8 and the further protease of step (a) with a substrate capable of being cleaved by DPP8 and the further protease, in conditions sufficient for cleavage of the substrate by DPP8 and the further protease; and (c) detecting substrate not cleaved by DPP8, but cleaved by the further protease, to identify that the molecule is capable of inhibiting specifically, the cleavage of the substrate by DPP8.

In a seventh aspect, the invention provides a method of reducing or inhibiting the catalytic activity of DPP8, the method comprising the step of contacting DPP8 with an inhibitor of DPP8 catalytic activity. As various inhibitors of DPPIV catalytic activity are shown herein to inhibit DPP8 catalytic activity, it is recognised that other inhibitors of DPPIV may be useful for inhibiting DPP8 catalytic activity. Examples of inhibitors suitable for use in the seventh aspect are described in [21,32,33]. Other inhibitors useful for inhibiting DPP8 catalytic activity can be identified by the methods of the fifth or sixth aspects of the invention, which methods are exemplified herein.

In one embodiment, the catalytic activity of DPP8 is reduced or inhibited in a mammal by administering the inhibitor of DPP8 catalytic activity to the mammal. It is recognised that these inhibitors have been used to reduce or inhibit DPPIV catalytic activity in vivo, and therefore, may also be used for inhibiting DPP8 catalytic activity in vivo. Examples of inhibitors useful for this purpose are disclosed in the following [21,32–34].

Preferably, the catalytic activity of DPP8 in a mammal is reduced or inhibited in the mammal, for the purpose of treating a disease in the mammal. Diseases which are likely to be treated by an inhibitor of DPP8 catalytic activity are those in which DPPIV-like gene family members are associated [3,10,11,17,21,36], including for example, neoplasia, type II diabetes, cirrhosis, autoimmunity, graft rejection and HIV infection.

Preferably, the inhibitor for use in the seventh aspect of the invention is one which inhibits the cleavage of a peptide bond C-terminal adjacent to proline. As described herein, examples of these inhibitors are 4-(2-aminoethyl) benzenesulfonylfluoride, aprotinin, benzamidine/HCl, Ala-Pro-Gly, H-Lys-Pro-OH HCl salt and zinc ions, for example, zinc sulfate or zinc chloride. More preferably, the inhibitor is one which specifically inhibits DPP8 catalytic activity, and which does not inhibit the catalytic activity of other serine proteases, including, for example DPPIV or FAP.

In an eighth aspect, the invention provides a method of cleaving a substrate which comprises contacting the substrate with DPP8 in conditions sufficient for cleavage of the substrate by DPP8, to cleave the substrate. Examples of molecules which can be cleaved by the method are H-Ala-Pro-pNA, H-Gly-Pro-pNA and H-Arg-Pro-pNA. The conditions sufficient for cleaving the substrate are described herein. Molecules which are cleaved by DPPIV including RANTES, eotaxin, macrophage-derived chemokine, stromal-cell-derived factor 1, glucagon and glucagon-like peptides 1 and 2, neuropeptide Y, substance P and vasoactive peptide are also likely to be cleaved by DPP8 [11,12]. In one embodiment, the substrate is cleaved by cleaving a peptide bond C-terminal adjacent to proline in the substrate. The molecules cleaved by DPP8 may have Ala, or Trp, Ser, Gly, Val or Leu in the P1 position, in place of Pro [11,12].

As described herein, DPP8 gene expression is upregulated in stimulated lymphocyte and lymphocytic cell lines which suggests that DPP8 may have a functional role in T cell costimulation and proliferation. It is recognised therefore that measuring DPP8 gene expression is useful for detecting T cell activation. Thus in a ninth aspect, the invention provides a method of detecting an activated T cell, the method comprising the step of detecting the level of DPP8 gene expression in a T cell. In one embodiment, the level of DPP8 gene expression is detected by measuring the amount of DPP8 mRNA in the cell, as described herein.

The inventors have characterised the sequence of a nucleic acid molecule which encodes the amino acid sequence shown in SEQ ID NO:1. Thus in a tenth aspect, the invention provides a nucleic acid molecule which encodes the amino acid sequence shown in SEQ ID NO:1.

In an eleventh aspect, the invention provides a nucleic acid molecule which consists of the sequence shown in SEQ ID NO:2.

As described herein, at least three splice variants of DPP8 RNA which have an open reading frame from 2.6 to 3.1 kb in length are observed. As a frame shift mutation or termination signal was not observed in the sequence of these splice variants, and as the coding sequence of two of the splice variants includes a sequence which encodes the amino acid sequence associated with catalytic activity, it is recognised that some of the peptides encoded by the splice variants are likely to have the substrate specificity of DPP8. Thus in an embodiment, the nucleic acid molecule is a fragment of the sequence shown in SEQ ID NO: 1 which is about 2.6 to 3.1 kb in length and which encodes a peptide which has the substrate specificity of the sequence shown in SEQ ID NO:1. Preferably, the nucleic acid molecule has a sequence shown in any one of SEQ ID NO.s: 4, 6 and 8.

In a twelfth aspect, the invention provides a nucleic acid molecule which is capable of hybridising to a nucleic acid molecule consisting of the sequence shown in SEQ ID NO:2 in stringent conditions, and which encodes a peptide which has the substrate specificity of the sequence shown in SEQ ID NO:1. As shown in the Northern blot analysis described herein, DPP8 mRNA hybridises specifically to the sequence shown in SEQ ID NO:2, after washing in 2×SSC/1.0%SDS at 37° C., or after washing in 0.1×SSC/0.1% SDS at 50° C. "Stringent conditions" are conditions in which the nucleic acid molecule is exposed to 2×SSC/1.0% SDS. Preferably, the nucleic acid molecule is capable of hybridising to a molecule consisting of the sequence shown in SEQ ID NO:2 in high stringent conditions. "High stringent conditions" are conditions in which the nucleic acid molecule is exposed to 0.1×SSC/0.1%SDS at 50° C.

As described herein, the inventors believe that the gene which encodes DPP8 is located at band q22 on human chromosome 15. The location of the DPP8 gene is distinguished from genes encoding other prolyl oligopeptidases, which are located on chromosome 2, at bands 2q24.3 and 2q23, or chromosome 7. Thus in an embodiment, the nucleic acid molecule is one capable of hybridising to a gene which is located at band q22 on human chromosome 15.

It is recognised that a nucleic acid molecule which encodes the amino acid sequence shown in SEQ ID NO:1, or which comprises has the sequence shown in SEQ ID NO:2, could be made by producing the fragment of the sequence which is translated, using standard techniques [30,31]. Thus in an embodiment, the nucleic acid molecule does not contain 5' or 3' untranslated sequences.

In a thirteenth aspect, the invention provides a vector which comprises a nucleic acid molecule of the tenth aspect of the invention. In one embodiment, the vector is capable of replication in a COS-7 cell, CHO cell or 293T cell, or E.coli. In another embodiment, the vector is selected from the group consisting of λTripleEx, pTripleEx, pGEM-T Easy Vector, pSecTag2Hygro, pet15b, pEE14. HCMV.gs and pCDNA3.1/V5/His.

In a fourteenth aspect, the invention provides a cell which comprises a vector of the thirteenth aspect of the invention. In one embodiment, the cell is an E. coli cell. Preferably, the E. coli is MC1061, DH5α, JM109, BL21DE3, pLysS. In another embodiment, the cell is a COS-7, COS-1, 293T or CHO cell.

In a fifteenth aspect, the invention provides a method for making a peptide of the first aspect of the invention comprising, maintaining a cell according to the fourteenth aspect of the invention in conditions sufficient for expression of the peptide by the cell. The conditions sufficient for expression are described herein. In one embodiment, the method comprises the further step of isolating the peptide.

In a sixteenth aspect, the invention provides a peptide when produced by the method of the fifteenth aspect.

In a seventeenth aspect, the invention provides a composition comprising a peptide of the first aspect and a pharmaceutically acceptable carrier.

In an eighteenth aspect, the invention provides an antibody which is capable of binding a peptide according to the first aspect of the invention. The antibody can be prepared by immunising a subject with purified DPP8 or a fragment thereof according to standard techniques [35]. As described herein, an antibody was prepared by immunising with transiently transfected DPP8+ cells. It is recognised that the antibody is useful for inhibiting activity of DPP8, or for detecting increased gene expression of DPP8, for the purpose of identifying an activated T cell. In one embodiment, the antibody of the eighth aspect of the invention is produced by a hybridoma cell.

In a nineteenth aspect, the invention provides a hybridoma cell which secretes an antibody of the nineteenth aspect.

BRIEF DESCRIPTION OF THE FIGURES

FIG. 2. Nucleotide sequence and amino acid sequence of human DPP8. The nucleotide and predicted one letter code amino acid sequence are shown. This sequence shows no putative membrane spanning domain (deduced from hydrophobicity plots) or potential N-linked glycosylation sites. The putative serine recognition site and aspartic acid and histidine which form the Ser-Asp-His catalytic triad are marked. Base pairs are numbered in the right margin.

FIG. 4a. Master RNA (CLONTECH) blot of poly A$^+$ RNA was hybridized with a $^{32}$p labelled DPP8 probe at 65° C. and washed at high stringency. The autoradiograph was exposed for 3 days at −70° C. with BIOMAX MS screen. DPP8 mRNA was detected in all tissues examined.

DETAILED DESCRIPTION OF THE INVENTION

EXAMPLES

General

Figure 1:
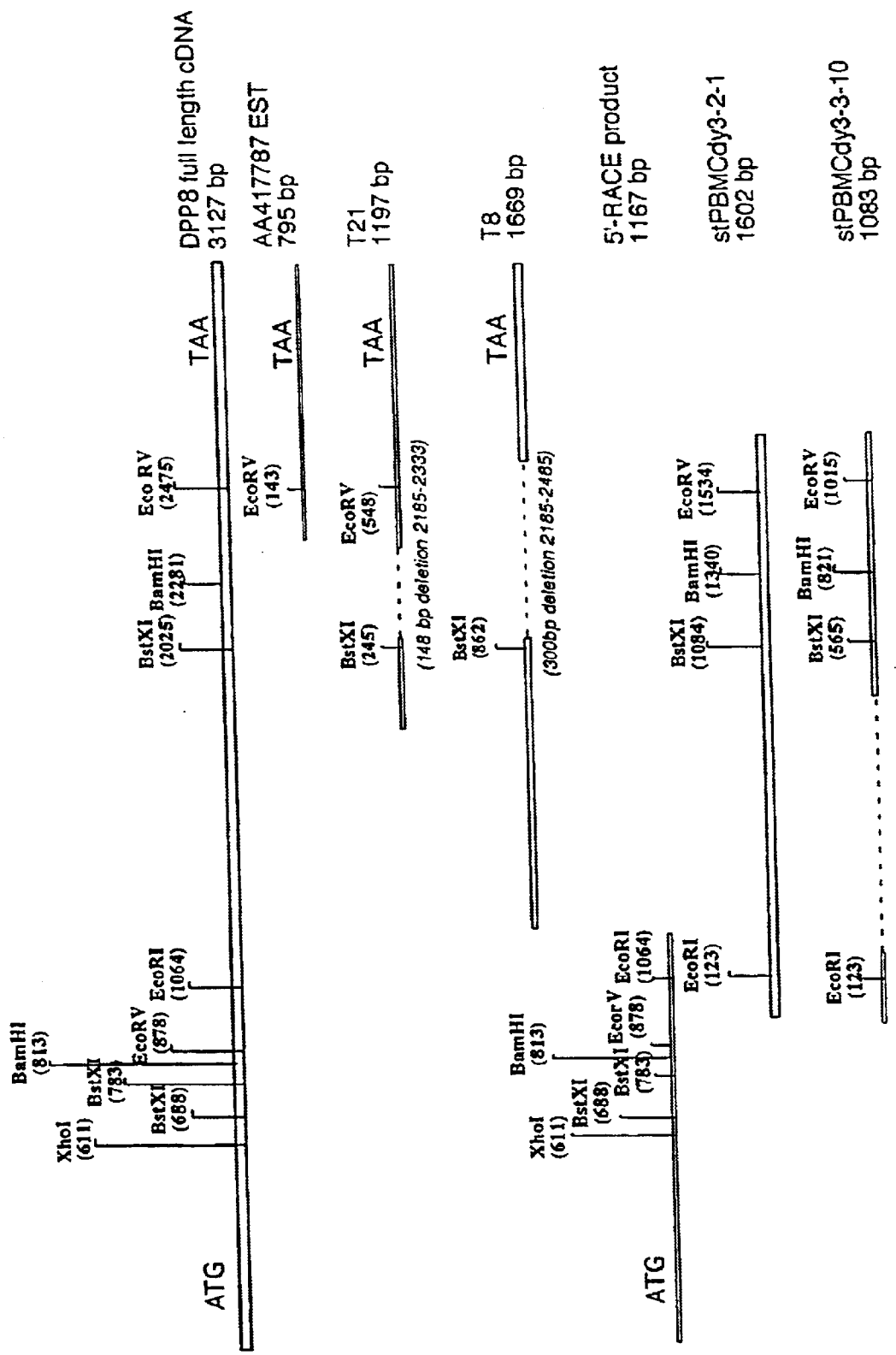
FIG. 1. Cloning strategy for isolating full-length DPP8 cDNA and the alternative splicing variants of DPP8 observed. Representation of three splice variants is shown including loss of serine recognition site by one splice variant (T8).

Restriction enzymes and other enzymes used in cloning were obtained from Boehringer Mannheim Roche. Standard molecular biology techniques were used [31] unless indicated otherwise.

An EST clone (GENBANK™ accession number AA417787) was obtained from American Type Culture Collection. The DNA insert of this clone was sequenced on both strands using automated sequencing at SUPAMAC (Sydney, Australia).

Cell Culture and RNA Preparation

Human peripheral blood monocytes (PBMCs) were isolated by Ficoll-Hypaque density-gradient centrifugation (Pharmacia, Uppsala, Sweden) of blood obtained from healthy donors. The PBMCs were incubated in AIM-V medium (Life Technologies, Gaithersburg, Md., USA) supplemented with 2 mM L-glutamine and were stimulated with either 1 $\mu$g.mL$^{-1}$ phytohaemagglutinin (Wellcome) or 100 ng.mL$^{-1}$ OKT3 (Orthoclone, Fla., USA) for 72 h. The human cell lines Jurkat, CCRF-CEM, Raji, Daudi and HepG2 were grown to confluence in Dulbecco's modified Eagle's medium (Trace Biosciences, NSW, Australia) supplemented with 10% fetal bovine serum and 2 mM L-glutamine.

Liver and placental RNA were prepared from snap-frozen human tissue as described previously [37]. However, RNA was prepared from PBMCs and cell lines using an RNAeasy kit (Qiagen, Germany).

Bioinformatics

BLAST programs [38] and all multiple sequence alignments were performed through the Australian National Genomic Information Service (ANGIS, Sydney, NSW, Australia). PILEUP (GCG Version 8, Genetics Computer Group, Madison, Wis., USA) was used for multiple sequence alignments of proteins.

A BLAST search was performed on the public expressed sequence tag (EST) database using the complete human DPPIV (GenBankwm™ accession number X60708) and FAP (accession number U09278) nucleotide sequences as query sequences. An EST clone (accession number AA417787) was obtained from the American Type Culture Collection. The DNA insert of this clone was sequenced on both strands using automated sequencing at SUPAMAC (Sydney, NSW, Australia). Because of its homology with DPPIV, this new gene was named dipeptidyl peptidase 8 (DPP8).

DPP8 Cloning

ESTAA417787 was used to design forward (caa ata gaa att gac gat cag gtg) and reverse (tct tga agg tag tgc aaa aga tgc) DPP8 primers for polymerase chain reaction (PCR) from ESTAA417787. The PCR conditions were as follows: 94° C. for 5 min, followed by 35 cycles of 94° C. for 1 minute, 55° C. for 30 sec and 70° C. for 1 min. This 484 bp PCR product was gel purified, $^{32}$P-α labelled using Megaprime Labeling Kit (Amersham Pharmacia Biotec, UK) and hybridized to a Master RNA blot (CLONTECH, Palo Alto, Calif., USA) that contained poly A$^+$ from 50 adult and fetal tissues immobilized in dots as per manufacturers' instructions. This Master RNA blot was also probed with DPP4 for comparison of mRNA tissue expression.

The forward and reverse DPP8 primers were used for PCR to screen a human placental λ STRETCH PLUS library (CLONTECH, Palo Alto, Calif., USA) for the presence of DPP8 cDNA in the library. The library was then screened by standard molecular biology techniques [30,31]. After primary screening, 23 clones were selected for secondary screening, after which 22 remained positive. For the tertiary screen the clones contained in λTriplEx were converted into pTriplEx plasmids and transformed into BM25.8 E. coli recipient bacteria. The plated bacteria were screened and it was confirmed that all 22 clones were positive. Two of these clones, T8 and T21 were selected for further study.

5' RACE (Rapid Amplification of cDNA Ends)

A 5' RACE Version 2.0 kit (Gibco BRL, Life technologies) was applied on activated T cell (ATC) and placental RNA as prescribed in the kit instructions. The T8 DNA sequence was used to design GSP 1 (TCC TTC CTT CAG CAT CAA TC) and GSP2 (CTT AAA AGT GAC TTT AGG ATT TGC TGT ACC). 5' RACE PCR products were cloned into PGEM-T Easy® Vector (Promega Co., Madison, Wis., USA) and sequenced by primer walking.

Confirmation of Identity of RACE Product

Reverse transcriptase PCR was carried out on ATC RNA using DPP8-pr23 (GGA AGA AGA TGC CAG ATC AGC TGG) and DPP8-prl9r (TCC GTG TAT CCT GTA TCA TAG AAG) to span across the junction between the RACE product and the EST and library clones. Two gel purified products ATCd3-2-1 (1603bp) and ATC3-3-10 (1077bp) were cloned into PGEM-T Easy® (Promega Co., Madison, Wisc., USA) and sequenced.

Subcloning of DPP8 cDNA into a pcDNA3.1/V5/His Expression Vector

The ATC RACE product, the ATCd3-2-1 (1603bp) junction fragment and the library clone T21 were joined together and cloned into the expression vector pcDNA3.1/V5/His A (Invitrogen, the Netherlands) to form a DPP8 cDNA of 3.1 kb with an open reading frame of 882 aa. The first construct was made using three sequential cloning steps. Firstly, a Eco RV/Xba I fragment of T21 (containing 3' DPP8, stop codon and 3' untranslated region on DPP8 cDNA) was ligated into the vector pcDNA3.1/V5/His A which had been digested with Eco RV/Xba I. An Eco RI/Eco RV fragment of ATCd3-2-1 was then added to this construct digested with Eco RI/Eco RV. Finally the RACE product was cut with Eco RI and cloned into the Eco RI site of the previous construct to form the complete 3.1 kb DPP8 cDNA. This construct pcDNA3.1-DPP8 expressed protein with no detectable tag. In addition the stop codon in the DPP8 expression construct in pcDNA3.1/V5/His V5 was genetically altered using PCR to create a C-terminal fusion with the V5 and His tag contained in the vector. This construct was named pcDNA3.1- DPP8/V5/His. All expression constructs subcloned into pcDNA3.1/V5/His were verified by full sequence analysis.

DPP8 Gene Expression by Northern Blot

Human multiple tissue Northern blots (CLONTECH) containing 2 ug of poly A$^+$ RNA were prehybridized in Express Hybridization solution (CLONTECH) for 30 min at 68° C. Both the DPP8 484 bp product and the 5' RACE ATC product were radiolabeled using a Megaprime Labeling kit (Amersham Pharmacia Biotech) and [$^{32}$P]dCTP (NEN Dupont). Unincorporated label was removed using a NICK column (Amersham Pharmacia Biotech) and the denatured probe was incubated for 2 hrs at 68° C. in Express Hybridization solution. Washes were performed at high stringency and blots exposed to BIOMAX MS film for overnight with a BIOMAX MS screen at −70° C.

DPP8 Gene Expression in Mice by Northern Blot

A Northern blot containing 10 ug of total liver RNA per lane was made using standard methods [31]. The RNA was derived from male and female mice of two strains, C57Bl6 and Balb/c. The Northern blot was prehybridized in Express Hybridization solution (CLONTECH, Palo Alto, USA) for 1 hr at 60° C. A 2.4 kb human DPP8 cDNA (PCR product) was radiolabeled using the Megaprime Labeling kit (Amersham Pharmacia Biotech) and [$^{32}$P]dCTP (NEN Dupont). Unincorporated label was removed using a NICK column (Amersham Pharmacia Biotech) and the denatured probe was incubated with the blot overnight at 60° C. in Express Hybridization solution. Washes were performed at low stringency (2×SSC/0.05% SDS for 1 h at 37° C. followed by 0.1×SSC/0.1% SDS for 30 min at 40° C.) and blots exposed to BIOMAX MS film for three days with a BIOMAX MS screen at −70° C.

Expression of DPP8 in Mouse Liver Using rtPCR

Mouse liver RNA was reverse transcribed using the Superscript II enzyme kit (Gibco BRL, Gaithersburg, Md.) as described previously [42]. The cDNA was diluted 1 in 4 and stored in aliquots at −70° C. PCR using mouseDPP8-prlF (atg att acc acc cag gaa gcg) as the forward primer and mouseDPP8-pr2R (atc tcc gac atc ttg aaa gtg acc) as the reverse primer was used to detect mouse DPP8 mRNA.

One ul of diluted cDNA was amplified in a 50 ul PCR reaction which contained: 0.2 mM dNTPs, 1 ul of 50×Advantage 2 Polymerase Mix (Clontech), 1×Advantage 2 PCR buffer (Clontech) and 100 ng of each primer. The PCR involved an initial step of 95° C. for 1 min to inactivate the TaqStart Antibody. This was followed by 35 cycles; denaturation at 95° C. for 30 sec, 68° C. for 1 min, followed by a final step of 68° C. for 1 min. The amplified products were analysed by electrophoresis of 10 µl of PCR reaction on a 3:1 Nusieve gel (FMC Bioproducts, Rockville, Md.) plus 0.5 µg/ml ethidium bromide in TAE buffer (0.04M Tris acetate, 0.001 M EDTA, pH 8.0). The gel was then Southern Blotted using standard techniques [31]. The Southern blot was hybridized at 60° C. for 2 hr with the 2.4 kb human DPP8 cDNA probe prepared as described above. Washes were performed at low stringency (2×SSC/0.05% SDS for 1 h at 37° C. followed by 0.1×SSC/0.1% SDS for 40 min at 50° C.). The blot was exposed to XAR5 Kodak film for 30 min at RT.

DPP8 Expression by RT-PCR

Reverse transcriptase PCR was performed on human ATC RNA, human placental RNA and human liver RNA using TED primers DPP8/pr3 (GCA CTA CCT TCA AGA AAA CCT TGG) and DPP8/pr20R (TAT GGT ATT GCT GGG TCT CTC AGG) to give a 293 bp product.

Transfection, Western blot, Immunocytochemistry, Cytochemistry and Flow Cytometry Monkey kidney fibroblast (COS-7) cells (American Type Culture Collection, CRL-1651) were grown and transfected as described previously [39]. For making stable cell lines, Geneticin (G418; Gibco-BRL) was added to the medium, beginning 24 h after transfection. COS cell extracts were prepared by sonication followed by differential centrifugation and neither boiled nor reduced before SDS/PAGE (10% gel) and transfer to nitrocellulose, as described previously [40,9]. The presence of DPP8 fused with the V5 epitope was detected using an anti-V5 mAb (Invitrogen). COS cell monolayers were fixed in cold ethanol before staining with anti-V5 mAb [39,41,9]. Some monolayers were fixed in 4% paraformaldehyde and permeabilized with 0.1% Triton X-100 [35], then double-stained with wheat germ agglutinin to label Golgi apparatus and with goat anti-mouse IgG to label DPP8, conjugated to Alexa Fluor 488 and Alexa Fluor 594, respectively (Molecular Probes, Eugene, Oreg., USA). Flow cytometry and confocal scanning microscopy using a Leica TCS-NT confocal microscope have been described previously [39,9].

Purification of Recombinant DPP8/V5/His and DPPIV/V5/His

Cells ($1 \times 10^7$) expressing each protein were sonicated in native buffer (50 mM sodium phosphate, 300 mM NaCl), then treated with 700 U DNAse for 20 min at room temperature. DPPIV is expressed at the cell surface, so 1% Triton X-100 was used to solubilize DPPIV/V5/His. Insoluble material was removed by centrifugation. The supernatant was incubated with 1 mL Talons® Metal Affinity Resin (Clontech) following the manufacturer's instructions for a batch/gravity flow procedure. The resin was washed with 50 mM sodium phosphate, containing 300 mM NaCl and 5 mM imidazole, and proteins were eluted using the same buffer containing 150 mM imidazole. Enzyme activity was used to monitor eluted fractions.

Enzyme Assays

Enzyme assays were performed as described previously [1]. Either clarified cell extract from $1 \times 10^4$ sonicated COS-7 cells or purified protein derived from $1 \times 10^5$ cells was incubated with substrate in 70 μL phosphate buffer, pH 7.4, for 30 min at 37° C., except where otherwise indicated. The specific DPPIV substrates, Gly-Pro-toluenesulfonate, H-Gly-Pro-p-nitroanilide (NA)/HCl (Sigma, St Louis, Mo., USA) and Gly-Pro-7-amino-4-trifluromethylcoumarin (Calbiochem, San Diego, Calif., USA) were tested. Other substrates tested were H-Ala-Pro-pNA/HCl, H-Arg-Pro-pNA acetate salt, H-Lys-Ala-pNA.2HCl, H-Asp-Pro-pNA, H-Ala-Ala-pNA/HCl, H-Ala-Ala-Pro-pNA/HCl, H-Ala-Ala-Phe-pNA, succinyl-Ala-Pro-pNA, H-Ala-Phe-Pro-pNA and Z-Ala-Pro-p-NA from Bachem (Switzerland). H-Ala-Pro-4-methoxyβNA/HCl, Z-Lys-Pro-4-methoxyβNAformate salt, H-Lys-Pro-4-methoxyβNA/HCl, Z-Ala-Pro-4-methoxyβNA, H-Gly-Pro-βNA and H-His-Ser-4-methoxyβNAacetate salt (Bachem) were tested for their ability to stain unfixed transfected cells. All inhibitors were (see Table 2) incubated with each purified enzyme in phosphate buffer, pH 7.4, for is min before the addition of substrate. After the addition of 1 mM H-Ala-Pro-pNA substrate for purified DPP8 and 1 mM H-Gly-Pro-pNA substrate for purified DPPIV, samples were incubated for 60 min at 37° C. All enzyme assays were performed in triplicate.

Chromosomal Localization of DPP8 by Fluorescence in situ Hybridization (FISH) Analysis DPP8 was localized using two different probes, the DPP8 EST and the T8 clone. The probes were nick-translated with biotin-$C^{14}$-dATP and hybridized in situ at a final concentration of 10 ng/ul to metaphases from two normal males. The FISH method was modified from that previously described [37] in that chromosomes were stained before analysis with both propidium iodide (as counterstain) and DAPI (for chromosomal identification). Images of metaphase preparations were captured by a cooled CCD camera using the Cyto Vision Ultra image collection and enhancement system (Applied Imaging International Ltd). FISH signals and the DAPI banding pattern were merged for figure preparation.

Expression of DPP8 in Human Lymphocytes and Cell Lines

RNA (1 μg) was reverse-transcribed using the Superscript II enzyme kit (Gibco-BRL) as described previously [42]. PCR using DPP8-pr18 (CTGTGACGCCACTAATTATCTATG; SEQ ID NO: 18) as the forward primer and DPP8-pr26R (CCTAGAGAGGCTAGGGTATTCAAG; SEQ ID NO: 198) as the reverse primer was used to detect full-length DPP8 mRNA. The glyceraldehyde-3-phosphate dehydrogenase (G3PDH) control primer set was G3PDH for (ACCACAGTCCATGCCATCAC; SEQ ID NO: 20) and G3PDHrev (TCCACCACCCTGTTGCTGTA; SEQ ID NO: 21) to give a 470-bp product.

cDNA (diluted 1:4; 1μg) was amplified in a 25-μL PCR mixture which contained: 0.2 mM dNTPs, 0.125 unit Amplitaq Gold enzyme (Perkin-Elmer), 1×buffer II (Perkin-Elmer), 1.5 mM $MgCl_2$ and 100 ng $mL^{-1}$ each primer. The 35-cycle PCR was performed as follows: denaturation at 94° C. for 1 min, primer annealing at 55° C. for 30 s, and an extension step at 72° C. for 1 min. The amplified products were analyzed by electrophoresis of 15 μL PCR mixture on a 3:1 Nusieve gel (FMC Bioproducts, Rockville, Md., USA) plus 0.5 μg $mL^{-1}$ ethidium bromide in Tris/acetate/EDTA buffer (0.04 M Tris/acetate, 0.001 M EDTA, pH 8.0).

Anti-peptide Antibody

Methods followed are described in Current Protocols in Immunology [35]. Two peptides were chosen using the software MacVector to predict antigenicity. The two peptides were custom synthesized (Auspep, Melbourne) and conjugated to diptheria toxin (Auspep, Melbourne). Rabbits were immunized with both peptides and serum collected at time zero and after each injection (IMVS, Adelaide.

The two peptides used were:
PEPTIDE Name: TEDDA-N
SEQUENCE: CTGYTERYMGHPDQNEQG-NH2 (SEQ ID NO: 22).
This is amino acids 773 to 789, plus a Cys at the N-terminus.
PEPTIDE Name: TEDDR-C
SEQUENCE: GKPYDLQIYPQERHSC-NH2 (SEQ ID NO: 23).
This is amino acids 836 to 850, plus a Cys at the C-terminus.
These sequences were taken from the C-terminal portion of DPP8.

Monoclonal antibody to DPP8

Standard methods were used for antibody production [35]. Mice were immunized with $2 \times 10^7$ live COS-7 (African Green Monkey Kidney) cells that had been transiently transfected with the DPP8 cDNA in the pcDNA3 vector. The final immunisation was with CHO (Chinese Hamster Ovary) cells stably transfected with DPP8 cDNA in the pEE14 vector. Spleen cells were fused with a standard fusion partner, X63Ag8 myeloma cells. Hybridoma culture supernatants were tested by immunoperoxidase histochemistry on monolayers of the DPP8-transfected CHO cell line, using untransfected CHO cells as the negative control. Hybridomas that produced antibody activity were cloned.

Results

Molecular Cloning and Sequence Analysis of DPP8

The insert in ATCC EST AA417787 was 795 bp in length, containing 527 bp of coding sequence, a TAA stop codon and 258 bp of 3' noncoding sequence (FIG. 1).

The hybridization of the Master RNA blot revealed that the gene comprising ESTAA417787 has ubiquitous tissue expression, with high levels of expression in testis and placenta. Based on this expression pattern, a placental cDNA library was screened with a 484 bp PCR product produced by the forward and reverse DPP8 primers. Sequence homology analysis revealed that only 2 of 23 clones contained 5' sequence additional to the sequence of ESTAA417787. These cDNA clones were designated T8 and T21, and were 1669 bp and 1197 bp respectively (FIG. 1). In addition, comparison of these sequences to ESTAA417787 revealed that T8 cDNA lacked a 153 bp (51aa) region that was present in T21 cDNA and ESTAA417787. This deletion would result in the loss of the catalytic serine (GWSYGG) in T8 cDNA. Many of the other clones characterized appeared to contain unrelated sequence which are probably intronic sequences as a result of incomplete splicing.

The 5' RACE technique was utilized on both ATC RNA and placental RNA to obtain the 5' end of the DPP8 gene. The RACE product obtained from activated T cell RNA was 0.2 kb larger than that from placental RNA but otherwise identical (FIG. 1). The first methionine within a Kozak sequence was found 214 bp from the 5' end of the activated T cell RACE product. This 5'211 bp region was 70.5% GC rich and contained a number of potential promoter and enhancer elements (Sp1, Ap1 and ETF sites) and so was deduced to be the 5' flanking region of the DPP8 gene. In order to confirm the identity of the 5' RACE product as the 5' end of DPP8, RT-PCR was carried out to span across the junction between the RACE product and T8 cDNA library clone. The RT-PCR on ATC RNA produced two clones ATCd3-2-1 and ATC3-3-10 (FIG. 1). Compared to T8 and T21, both clones had an additional insert region of 144 bp (48 aa) immediately adjacent to the splice site of T8. Sequence homology analysis of this additional insert region found a homologous region in both the C. elegans homologue and DPP4. This clearly showed that T8 and T21 library clones represented splice variants of DPP8. The smaller clone ATCd3-3-10 was also found to represent another splice variant of DPP8 as it contained a 516 bp deletion at the 5' end which would result in a deletion of 175 aa.

Figure 2:
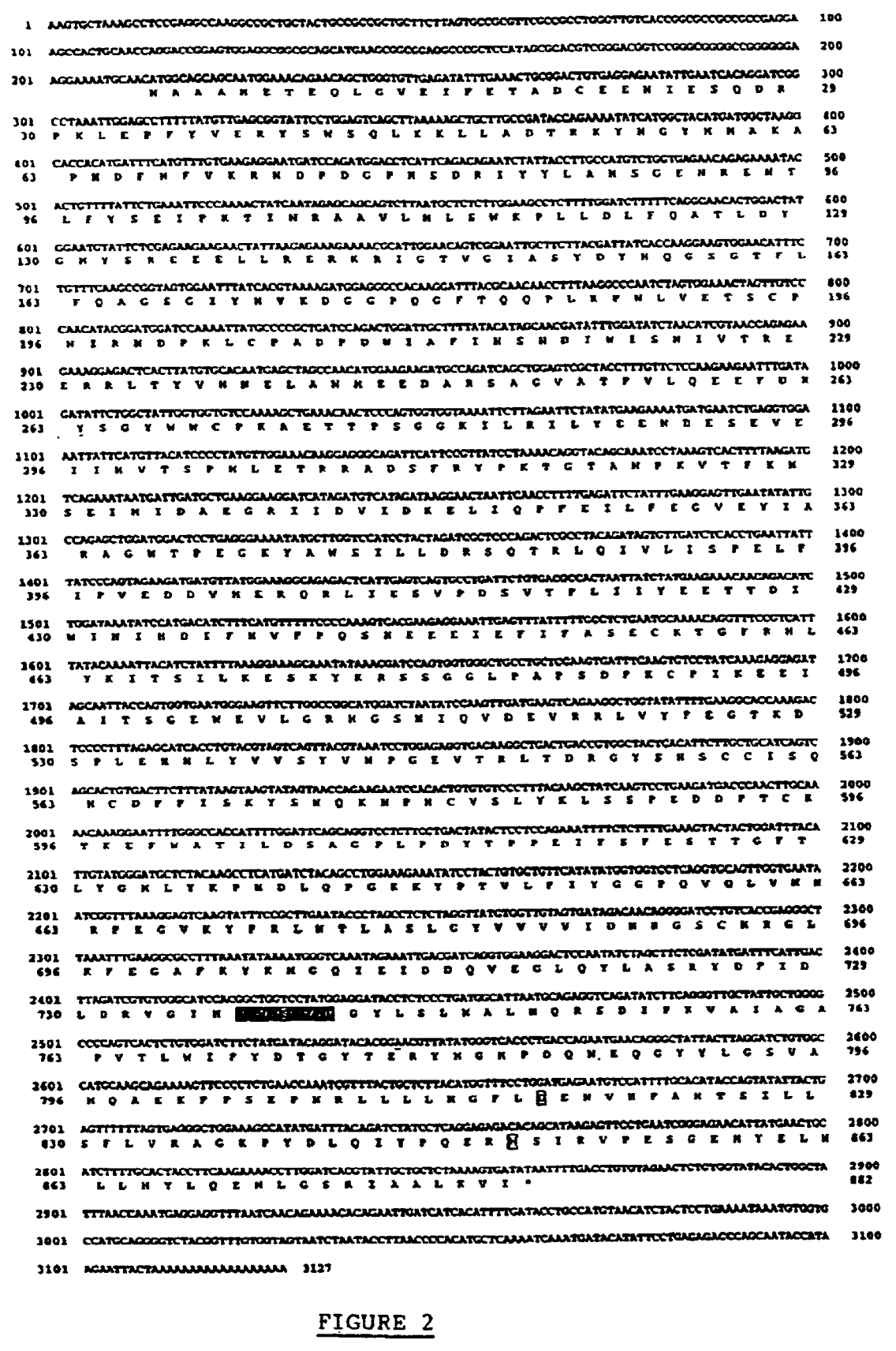
Figure 3:
FIG. 3. Alignment of the deduced amino acid residue sequence of DPP8 with the C. elegans homolog of DPP8 and human DPPIV. Amino-acid residues are numbered in the right margin. Amino-acid residues identical in all three proteins are boxed. Asterisks mark the putative catalytic triad residues and two glutamates of the β-propeller domain essential for DPPIV enzyme activity. The grey shading denotes the α/β hydrolase domain of these proteins. Filled triangles joined by lines indicate starts and ends of alternatively spliced transcripts, stPBMCdy3-3-10 (solid lines), T8(dashed lines) and T21 (solid lines). The alignment was constructed using the PILEUP program in GCG.

A full-length DPP8 clone was created using the larger RACE product, ATC3-2-1 and the T21 library clone. This generated a putative DPP8 cDNA of 3.1 kb (including 5' and 3' untranslated regions) with an open reading frame of 882 aa for further sequence analysis and examining DPP8 function. This 882 putative DPP8 protein contained no N-linked glycosylation sites and Kyte-Doolittle hydrophobicity analyses revealed it lacked a transmembrane domain, unlike DPP4, FAP and DPP6. Thus it is likely that DPP8 is a cytoplasmic protein (FIG. 2). The predicted DPP8 protein shared 51% amino acid similarity and 27% amino acid identity with human DPP4; the C termini of these proteins exhibited the most homology (FIG. 3).

Tissue Distribution of DPP8 as Determined by Master RNA and Northern Blot

A master RNA blot was probed with a 484 nt PCR product produced by the forward and reverse DDPB primers as mentioned previously. The rnRNA tissue expression of DPP8 was ubiquitous in all human adult and fetal tissues. A similar ubiquitous expression pattern was observed using DPP4 cDNA as a probe (data not shown). However, by visual assessment the greatest levels of expression using each gene specific probe were in different tissues. The most intense signals using the DPP8 probe were in testis followed by placenta whereas the most intense signals using the DPP4 probe were in salivary gland and prostate gland followed by placenta (data not shown). The probes did not bind any of the negative controls on the blot.

Figure 4:
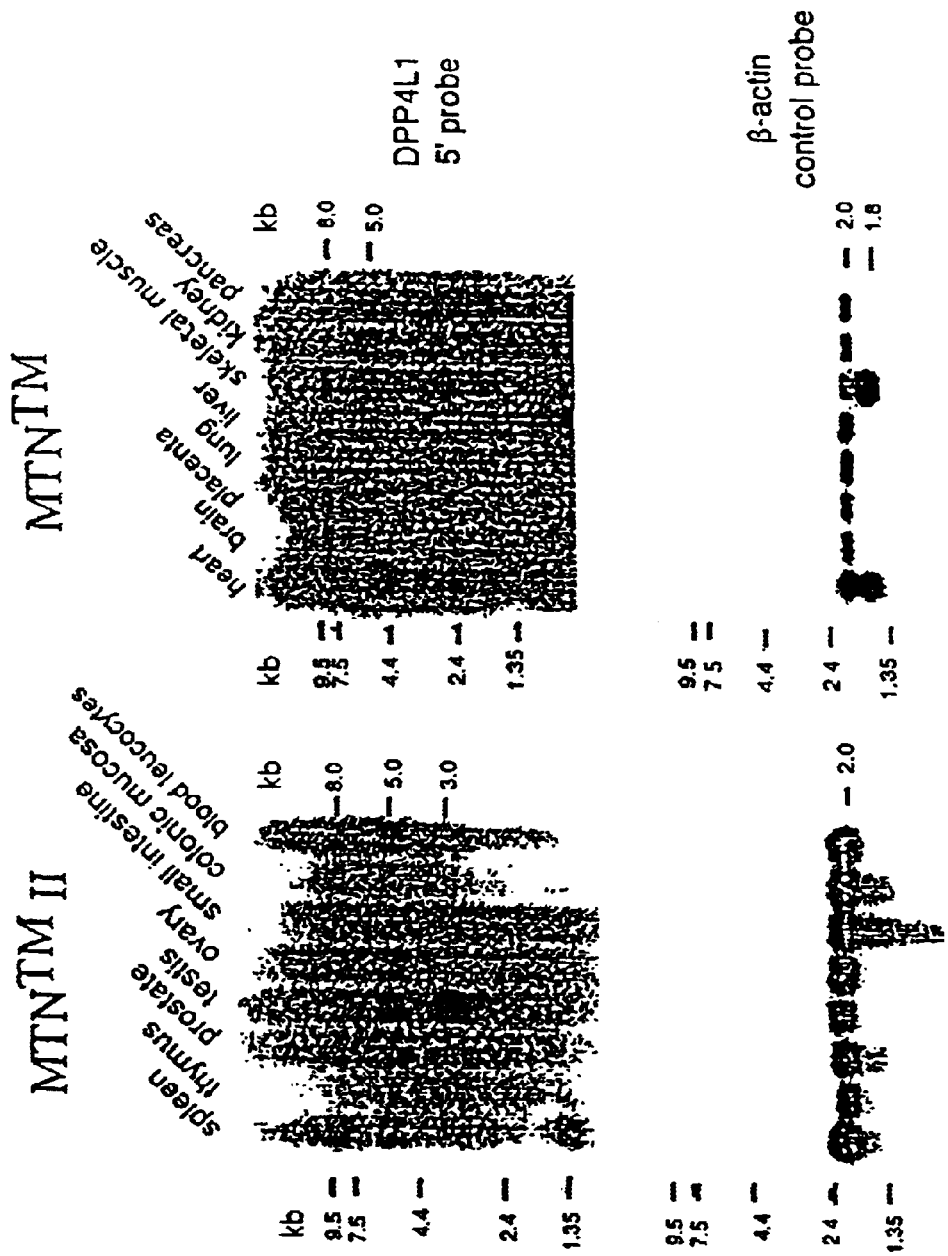
FIG. 4. Northern Blot analysis of DPP8 expression. Human multiple tissue Northern blots (CLONTECH) containing 2 $\mu$g per lane of poly A$^+$ RNA were hybridized with a $^{32}$p labeled DPP8 probe at 68° C. and washed at high stringency. The autoradiograph was exposed for 1 day at −70° C. with a BIOMAX MS screen. Molecular mass markers are indicated in base pairs on the left side of each autoradiogram.

Northern blot analysis was performed on mRNA derived from different human tissues (FIG. 4). Two DPP8 specific probes indicated the presence of transcripts in all tissues examined. A transcript approximately 3.0 kb in size consistent with the approximate expected size of DPP8 message was detected only in the testis. However, two transcripts of 8.0 and 5.0 kb respectively were present in testis, spleen, peripheral blood leukocytes and ovary at high levels; in prostrate, small intestine, and colonic mucosa at moderate levels; and in the thymus at lower levels. The Multiple tissue Northern blot was also probed with radiolabeled human β-actin probe and a common 2.0 kb transcript was seen in all tissues (FIG. 4).

Expression of DPP8 in Mice Determined by Northern Blot and rtPCR

Figure 9A:
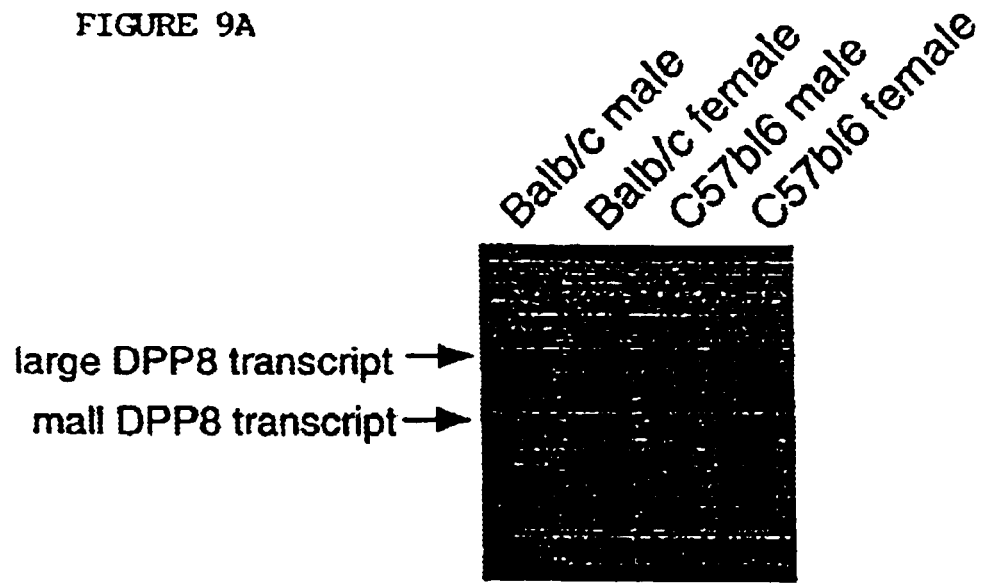
FIG. 9. Northern blot analysis of murine DPP8 expression. A murine Northern blot containing 10 $\mu$g per lane of total RNA was hybridized with a $^{32}$P-labeled human DPP8 probe at 60° C. and washed at low stringency. Autoradiographic exposure was for 3 days at −70° C. with a BIOMAX MS screen.
Figure 9B:
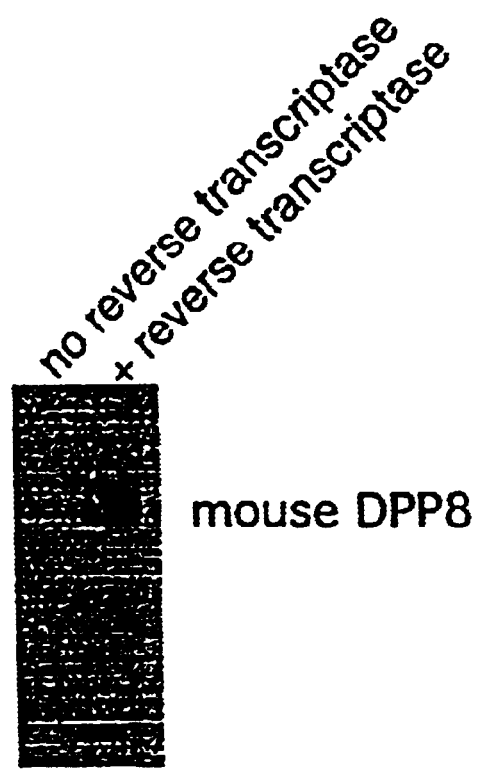

The human DPP8 cDNA sequence cross-hybridized with murine derived liver RNA. The Northern blot containing total RNA from mouse liver hybridized to a human DPP8 probe, showing that DPP8 mRNA is expressed in mouse liver (FIG. 9A). Two mRNA transcripts of murine DPP8 were present. This is a similar pattern to that observed for human DPP8. These transcripts probably represent different length 5' and 3' untranslated regions of the murine DPP8 gene. The presence of DPP8 mRNA in the mouse liver was also demonstrated using rt-PCR. The primers tested generated a 537 bp PCR product. A Southern blot of this product confirmed that the murine DPP8 cross-hybridizes with human DPP8 (FIG. 9B).

Expression and functional activity of DPP8

Figure 6:
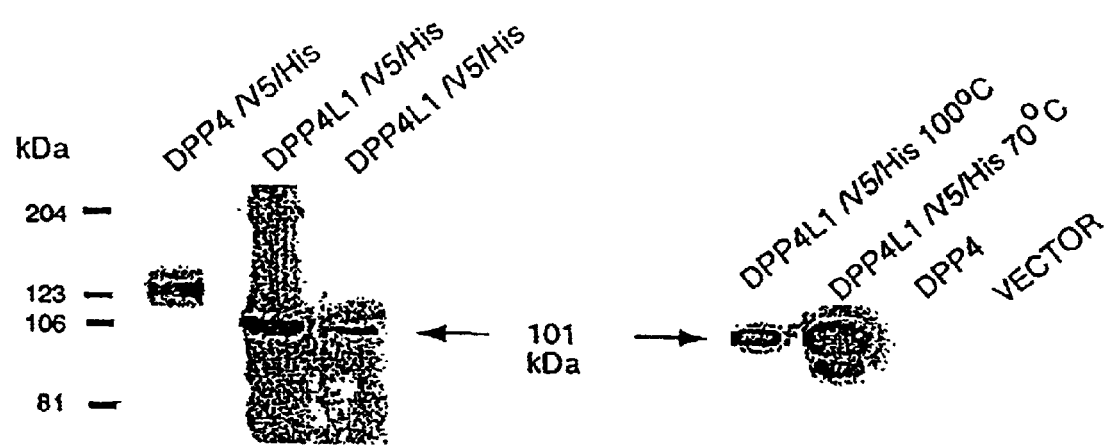
FIG. 6. Western blot analysis of transfected cell lines. Analysis of lysates of stable cell lines. DPP8 protein was seen in DPP8 /V5/His stable cell lines but not in DPP4 or vector-only stable cell lines. The electrophoretic mobility of the protein was not altered when samples were boiled. The band of greater mobility was probably a breakdown product of intact DPP8.
Figure 7:
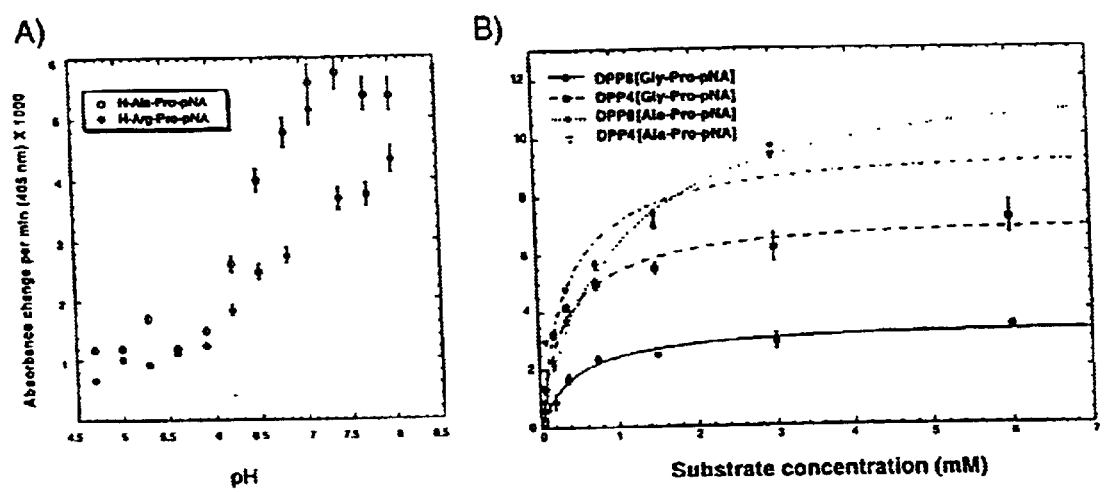
FIG. 7. DPP8 enzyme activity. (A) pH-dependence of DPP8 enzyme activity. (B) DPP8 and DPPIV enzyme kinetics. Means +/− SD of absorbance change per minute, multiplied by 1000 are shown. Curve fitting assumed Michaelis-Menten kinetics.

To assess the function of DPP8 protein, the full length DPP8 cDNA of 3.1 kb was cloned into the Xba I site of pcDNA3.1A/V5/His expression vector to produce two constructs. The first construct, pcDNA3.1-DPP8, expressed DPP8 protein on its own whilst the second construct, cDNA3.1-DPP8/V5/His expressed a protein with the V5 epitope and His tag fused to the C-terminus of DPP8 to facilitate analysis of protein expression. Mammalian expression constructs were stably transfected into COS-7 cells and cellular sonicates prepared. Consistent with the molecular weight predicted from the amino acid sequence a 100 kDa monomer was detected by western blotting of stable DPP8/V5/His expressing cells (FIG. 6). DPP8/V5/His protein was detected in the cytoplasmic compartment but not on the surface of ethanol fixed stable DPP8/V5/His expressing COS cells, using the anti-V5 mAb.

DPP8 is a Dipeptidyl Peptidase

Sequence homology between DPPIV and DPP8 suggested functional similarities, so cell lysates of DPP8-transfected cells were examined for proline-specific peptidase activity. DPPIV expressed in COS-7 cells with or without the V5/His tag were positive controls, and negative controls included vector-only transfected COS07 cells. Extracts of DPP8-transfected COS-7 cells hydrolyzed H-Ala-Pro-pNA and H-Arg-Pro-pNA but not H-Gly-Pro-pNA, H-Gly-Arg-pNA, H-Gly-Pro-toluenesulfonate or H-Gly-Pro-7-amino-4-trifluoromethylcoumarin above the levels exhibited by untransfected COS-7 cells (data not shown). The pH optimum of DPP8 enzyme activity was 7.4 (FIG. 5A), similar to the pH 7.8 optimum DPPIV enzyme activity [43,44]. DPP8 exhibited little activity below pH 6.3, suggesting that it is not an enzyme of the lysosome/endosome compartment. Of all the substrates tested on cell monolayers, only Ala-Pro-4MβNA/HCl stained DPP8-transfected COS cells and CHO cells (data not shown).

Both purified recombinant DPP8/V5/His and purified recombinant DPPIV/V5/His hydrolyzed H-Ala-Pro-pNA, G-Gly-Pro-pNA and H-Arg-Pro-pNA. Transfection with DPP8 possibly causes increased dipeptidase, tripeptidase and endopeptidase activities, similar to an effect of DPPIV transfection of melanoma cells [18]. Indeed, our results showed that DPP8 transfected COS-7 cells, but not purified recombinant DPP8, exhibited tripeptidyl peptidase activity using the substrate H-Ala-Ala-Pro-pNA and endopeptidase activity using the substrate Z-Ala-Pro-pNA (data not shown). This was investigated further, and neither of the tripeptidyl peptidase substrates H-Ala-Ala-Phe-pNA or H-Ala-Phe-Pro-pNA [45] nor the prolyl endopeptidase substrates Z-Ala-Pro-pNA or succinyl-Ala-Pro-pNA were cleaved by purified DPP8. Our data clearly demonstrate that DPP8 is a dipeptidyl peptidase and lacks tripeptidyl peptidase or endopeptidase activities.

The nature of the catalytic mechanism of DPP8 was further investigated using various inhibitors. DPP8 enzyme activity was significantly inhibited by serine proteinase inhibitors and was insensitive to inhibitors of metalloproteinases, aspartyl proteinases and cysteine proteinases. DPP8 enzyme activity was significantly inhibited by zinc, which completely inhibits DPPIV enzyme activity [46]. The peptides Ala-Pro-Gly and Lys-Pro mimic DPP8 substrates and probably competitively inhibited DPP8.

Chromosomal Localization of DPP8

Figure 5:
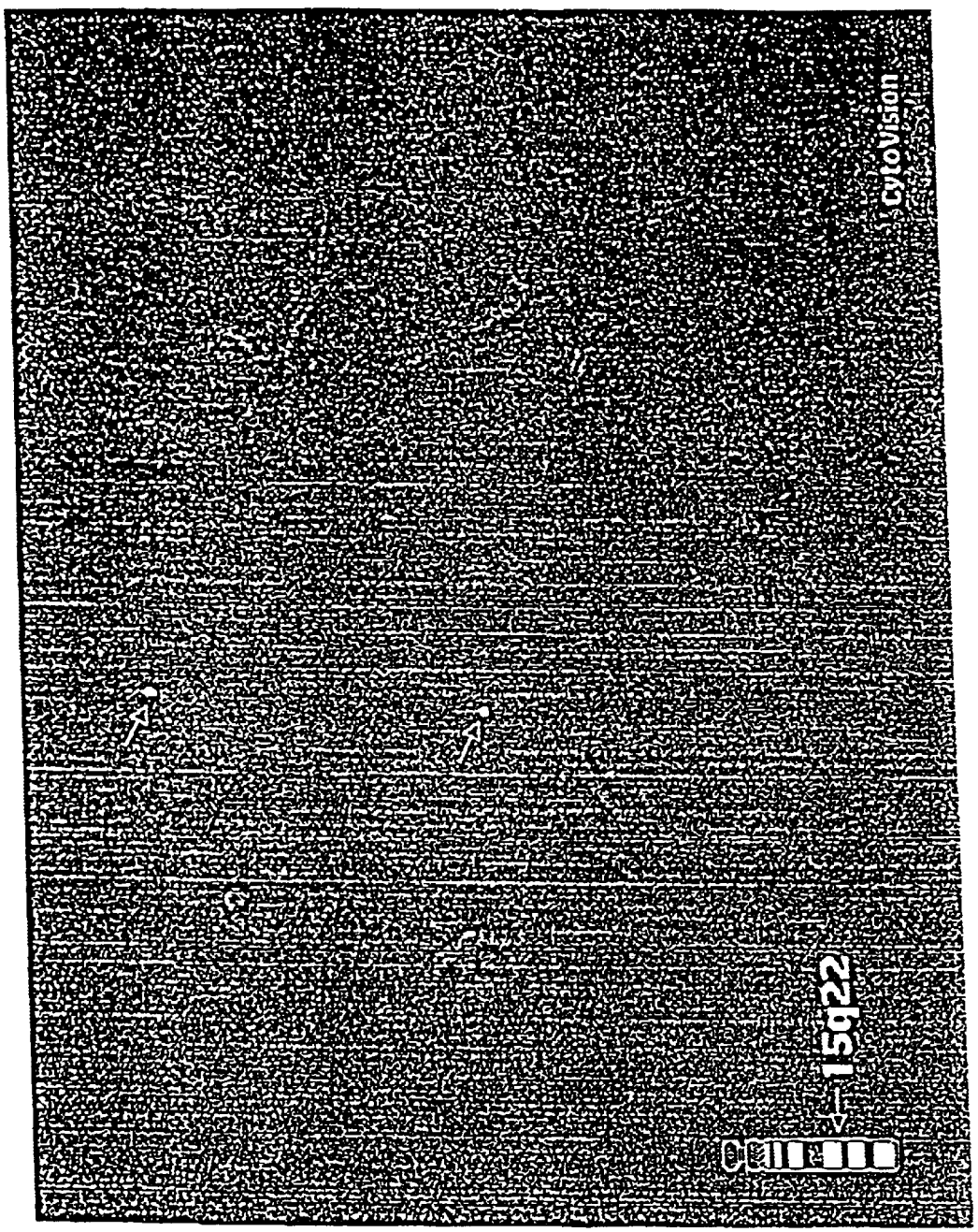
FIG. 5. Chromosomal localization of human DPP8. Metaphase showing FISH with the biotinylated DPP8 cDNA probe. Normal male chromosomes stained with DAPI. Hybridization sites on chromosome 15 are indicated by an arrow.

Two probes were used for FISH analysis, ESTAA417787 and the T8 clone from the placental library. Seventeen metaphases from the first normal male were examined for fluorescent signal. All of these metaphases showed signal on one or both chromatids of 15 at band q22 (FIG. 5). There were a total of 2 non-specific background dots observed in these metaphases. A similar result was obtained from the hybridization of the probe to 15 metaphases from the second normal male (data not shown).

Analysis of DPP8 Gene Expression by RT-PCR

Figure 8:
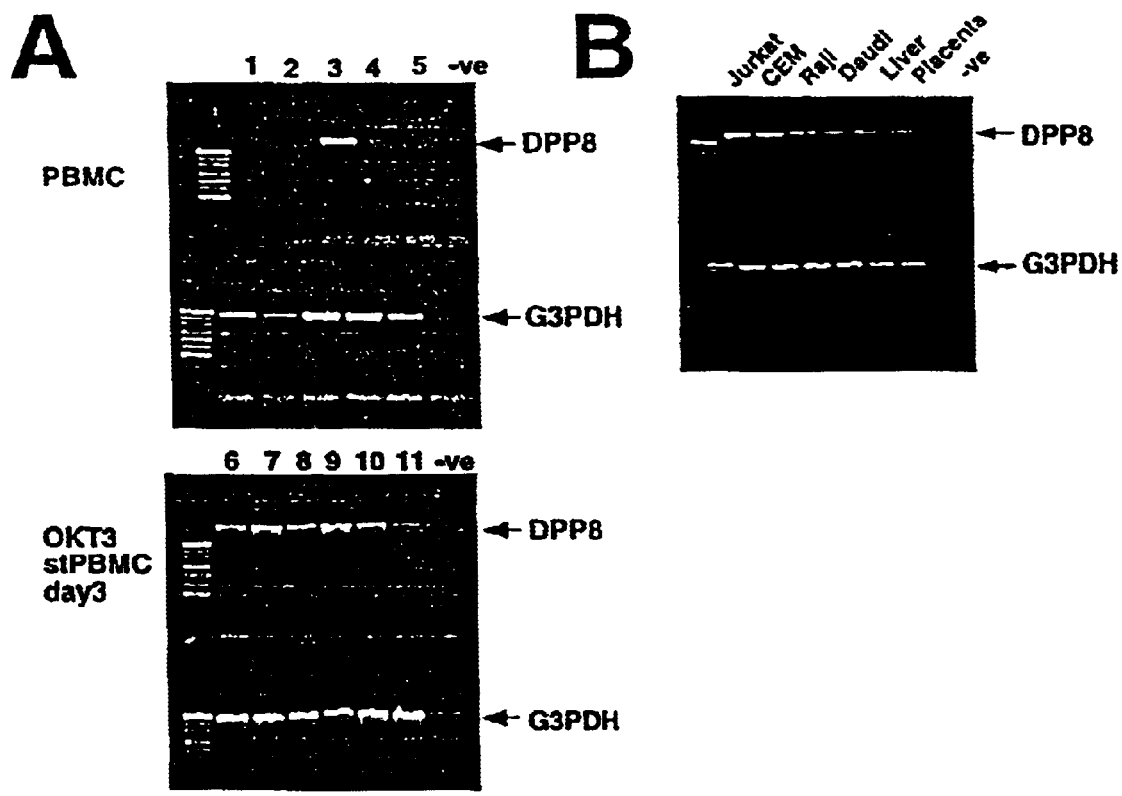
FIG. 8. RT-PCR analysis of DPP8 expression. PCR amplifications with primers specific for either a portion of human DPP8 that contained no alternate splicing, Val416 to Gly 679 (top of each gel) or glyceraldehyde-3-phosphate dehydrogenase (G3PDH) (bottom of each gel. (A) Top gel, lanes 1–5 contain PCR products from unstimulated PBMC cDNA from five subjects. Bottom gel, lanes 6 to 11 contain PCR products from OKT3-stimulated PBMC cDNA from six subjects. (B). PCR products are from cDNA from lymphocytic cell lines, liver or placenta as indicated. Negative control amplifications contained reaction mix, enzyme and no cDNA template. Each PCR was performed for 35 cycles. The PCR products were electrophoresed on agarose gels and stained with ethidium bromide. The left lane of each gel contains PUC19 digested with HaeIII as size markers.

DPPIV is expressed by most lymphocytes and lymphocytic cell lines but upregulated on activated lymphocytes [47, 41, 48, 49]. The various splice variants of DPP8 might not encode functional protein, so the PCR was designed to detect only mRNA that contained full-length sequence (FIG. 1). At 35 cycles, amplification product of the expected size (783 bp) was readily observed in OKT3-stimulated PBMCs (six of six subjects; FIG. 8) but not in unstimulated PBMCs from most subjects (four of five, FIG. 8A), suggesting that more DPP8 mRNA is expressed in activated T cells than in unstimulated PBMCs. Similar RT-PCR data were obtained from PBMCs stimulated with phytohaemagglutinin (data not shown). In addition, DPP8 mRNA was expressed in all B and T cell lines examined and in both liver and placenta (FIG. 8B).

Anti-peptide Antibody

The sera of two rabbits were tested by ELISA in peptide-coated wells. Both sera bound both peptides whereas the pre-immunisation serum samples did not exhibit specific binding. Western blots on extracts of cell lines, cell lines transfected with DPP8 cDNA and activated human lymphocytes showed that a rabbit antiserum to the two DPP8 peptides binds a 100 kDa band, which is the size of DPP8. (Data not shown).

TABLE 1

$K_m$ and $V_{max}$ values for DPP8 and DPPIV

| | $K_m$ (mM) | | $V_{max}$ ($\Delta A\ min^{-1} \times 1000$) | |
|---|---|---|---|---|
| | DPPIV | DPP8 | DPPIV | DPP8 |
| H-Ala-Pro-pNA | 0.374 ± 0.134 | 0.991 ± 0.171 | 9.6 ± 1.0 | 12.4 ± 0.9 |
| H-Gly-Pro-pNA | 0.347 ± 0.088 | 0.467 ± 0.064 | 7.2 ± 0.49 | 3.5 ± 0.14 |

Table 2. Inhibition of the peptidase activity of DPP8 in comparison with DPPIV. Common proteinase inhibitors of various enzyme types were incubated with the purified peptidases before assay with the substrates H-Ala-Pro-pNA on DPP8 or H-Gly-Pro-pNA on DPPIV. AEBSF, 4-(2-aminoethyl)benzenesulfonylfluoride.

TABLE 2

Inhibition of the peptidase activity of DPP8 in comparison with DPPIV. Common proteinase inhibitors of various enzyme types were incubated with the purified peptidases before assay with the substrates H-Ala-Pro-pNA on DPP8 or H-Gly-Pro-pNA on DPPIV. AEBSF, 4-(2-aminoethyl)benzenesulfonylfluoride.

| | | Residual activity (% of control) | |
|---|---|---|---|
| Type of inhibitor | Concentration | DPP8 | DPPIV |
| None | | 100 | 100 |
| Serine proteinase | | | |
| AEBSF | 4 mM | 40 | 52 |
| Aprotinin | 4 µg mL$^{-1}$ | 47 | 81 |
| Benzamidine/HCl | 10 mM | 82 | 89 |
| Peptides | | | |
| Gly-Gly-Gly | 10 mM | 99 | 106 |
| Ala-Pro-Gly | 10 mM | 51 | 67 |
| H-Lys-Pro-OH HCl salt | 4 mM | 63 | 45 |
| Zinc sulphate | 2 mM | 25 | 0 |
| Metalloproteinase | | | |
| EDTA | 2 mM | 115 | 99 |
| Aspartate(acidic) proteinase | | | |
| Pepstatin | 2 µg mL$^{-1}$ | 107 | 110 |
| Leupeptin | 0.1 mM | 93 | 104 |
| Cysteine(thiol) proteinase | | | |
| Iodoacetamide | 2 mM | 100 | 115 |
| Dithiothreitol | 2 mM | 108 | 109 |

Discussion

We describe the cloning, recombinant expression, biochemistry and tissue expression of a novel human DPPIV-related postproline peptidase that we have named DPP8. DPP8 exhibited dipeptidyl aminopeptidase but not tripeptidyl peptidase or endopeptidase activity. Like DPPIV, DPP8 was found to exhibit significant mRNA expression in activated T cells. Clear indications that DPP8 is a monomeric, nonglycosylated, soluble, cytoplasmic protein, which are characteristics of PEP but not of DPPIV, FAP or DPP6, were provided by our sequence and localisation data. DPP8 enzyme activity had a neutral pH optimum, suggesting that it is not active in the acidic lysosome/endosome compartment.

By homology with DPPIV, DPP8 is a member of the DPPIV-like gene family, a member of the prolyl oligopeptidase family S9b, and a member of the enzyme clan SC. The residues in DPP8 that potentially form the charge-relay system are Ser739, Asp817 and His849 (FIG. 2). The dipeptidyl peptidase activity of DPP8 and the absence of detectable tripeptidyl peptidase or endopeptidase activities by purified DPP8 further support its placement in the S9b family. Furthermore, the DPP8 substrate specificity was indistinguishable from that of the structurally related peptidases DPPIV and FAP.

The role of DPPIV in human lymphocytes has been studied in detail using enzyme inhibitors [49, 50–54]. DPPIV-specific inhibitors suppress both DNA synthesis and cytokine production in vitro [48, 49, 52]. In addition, DPPIV-specific inhibitors decrease phorbol myristate acetate-induced tyrosine phosphorylation in human lymphocytes, further suggesting a role for DPPIV enzyme activity in lymphocyte activation [54]. In vivo, inhibitors of DPPIV suppress arthritis [20] and prolong cardiac allograft survival in animal models [55]. The ability of DPP8 to cleave DPPIV substrates indicates that DPPIV inhibitors may also inhibit DPP8 and that inhibitor studies may require further interpretation. Indeed, DPP8 may be responsible for some of the physiological functions that have been assigned to DPPIV.

FAP and DPPIV are integral membrane glycoproteins and require dimerization for catalytic activity [19, 56, 57]. In contrast, DPP8 and PEP are non-glycosylated cytosolic proteins that are catalytically active as monomers [58] and cleave Pro-Xaa bonds [43,59]. However, the substrate specificity of PEP is distinct from DPP8. PEP is an endopeptidase that does not cleave if a free α-amine lies N-terminal to the proline (e.g. it does not cleave H-Ala-Pro). Recently we have proposed that the tertiary structure of DPPIV is similar to that of PEP in having a seven-blade β-propeller domain and an α/β-hydrolase domain [3, 39, 1]. The significant sequence identity between DPP8 and DPPIV indicates that the tertiary structures of DPP8 and DPPIV are similar. However, DPP8 contains 110 amino acids more than DPPIV, so it could have an additional element of tertiary structure such as an eighth propeller blade.

The ancestral relationships between DPP8, DPPIV and FAP are reflected in their chromosomal localization. While DPPIV and FAP have both been localized to the long arm of chromosome 2, 2q24.3 [601] and 2q23 [61] respectively, DPP8 was localized to 15q22. The related genes DPP6 and PEP have been localized to chromosome 7 [621] and 6q22 respectively [63].

Two human disease loci have been mapped to 15q22. These loci are an autosomal recessive deafness locus [64] and a form of Bardet-Biedl syndrome, type 4 [65]. Two of the clinical manifestations of Bardet-Biedl syndrome are obesity and diabetes. Attractin [66] and DPPIV have roles in obesity [67] and diabetes [22, 68, 15] respectively and as their substrate specificities overlap with that of DPP8, it is possible that DPP8 may be involved in Bardet-Biedl syndrome.

DPPIV is expressed on the surface of T cells and is a costimulatory molecule called CD26 [3]. CD26-negative cell lines have residual DPPIV enzyme activity and PBMC have non-DPPIV derived activity against Ala-Pro substrates [69], indicating the existence of other peptidase(s) with DPPIV-like activity. DPPIV-β exhibits a peptidase activity similar to DPPIV but is a 70–80 kDa cell surface glycoprotein [70] and is therefore distinct from DPP8.

The biological significance of the three splice variants of DPP8 that we discovered is unknown. None of these splice variants result in a frame shift or premature protein termination (FIG. 1). Two of the splice variants contain all the predicted catalytic triad residues and thus potentially produce proteins with peptidase activity. Alternate splice forms of FAP mRNA have also been observed [71, 72]. It is possible that expression of splice variants may be used to regulate the levels of active protein. DPP8 Northern blots revealed a number of differently sized transcripts. The predicted sizes of splice variants of DPP8 ranged from 2.6 to 3.1 kb whereas the large transcripts seen in most tissues examined in the Northern blots were 8.5 kb and 5.0 kb respectively. Similarly, two other members of the DPPIV-like gene family, DPPIV and DPP6, exhibit mRNA transcripts in Northern blots that are much larger than the cDNA size [60, 61]. We propose that the major transcripts for DPP8 mRNA and its splice variants lie within the 5 kb band while the 8.5 kb transcript(9) may contain additional 5' and 3' untranslated sequences. DPP8 appears to be like DPPIV in having a ubiquitous mRNA expression pattern by Northern analysis while being upregulated in activated T cells. The similarities between DPP8 and DPPIV suggest that DPP8 may, like DPPIV, play a role in T cell costimulation and proliferation. The development of DPP8 specific antibodies or inhibitors will facilitate work in this area.

In summary, we have identified and characterized a novel human dipeptidyl aminopeptidase DPP8 with structural and functional similarities to DPPIV and FAP. With many diverse biological roles suggested for DPPIV, particularly in the immune system, and the roles of FAP in tumor growth and liver disease, it will be interesting to investigate the roles of this new member of the DPPIV-like gene family in these systems. Further work in understanding this novel protein and the elucidation of inhibitors and physiological substrates will help identify the specific functions of individual members of this gene family.

References

1. Abbott C A, G W McCaughan & M D Gorrell 1999 Two highly conserved glutamic acid residues in the predicted beta propeller domain of dipeptidyl peptidase IV are required for its enzyme activity *FEBS Letters* 458: 278–84.
2. Abbott C A, D M T Yu, G W McCaughan & M D Gorrell 2000 Post proline peptidases having DP IV like enzyme activity *Advances in Experimental Medicine and Biology* 477: 103–9.
3. McCaughan G W, M D Gorrell, G A Bishop, C A Abbott, N A Shackel, P H McGuinness, M T Levy, A F Sharland, D G Bowen, D Yu, L Slaitini, W B Church & J Napoli 2000 Molecular pathogenesis of liver disease: an approach to hepatic inflammation, cirrhosis and liver transplant tolerance *Inmmunological Reviews* 174: 172–91.
4. Scanlan M J, B K Raj, B Calvo, P Garin-Chesa, M P Sanz-Moncasi, J H Healey, L J Old & W J Rettig 1994 Molecular cloning of fibroblast activation protein alpha, a member of the serine protease family selectively expressed in stromal fibroblasts of epithelial cancers *Proceedings of the National Academy off Sciences United States of America* 91: 5657–61.
5. Handbook of Proteolytic Enzymes. Barrett A J, N D Rawlings & J F Woess. 1998., London: Academic Press. 1666.
6. Jacotot E, C Callebaut, J Blanco, B Krust, K Neubert, A Barth & A G Hovanessian 1996 Dipeptidyl-peptidase IV-beta, a novel form of cell-surface-expressed protein with dipeptidyl-peptidase IV activity European *Journal of Biochemistry* 239: 248–58.

7. Rawlings N D & A J Barrett 1999 MEROPS: the peptidase database *Nucleic Acids Research* 27: 325–31.
8. Park J E, M C Lenter, R N Zimmermann, P Garin-Chesa, L J Old & W J Rettig 1999 Fibroblast activation protein: A dual-specificity serine protease expressed in reactive human tumor stromal fibroblasts Journal of *Biological Chemistry* 274: 36505–12.
9. Levy M T, G W McCaughan, C A Abbott, J E Park, A M Cunningham, E Muller, W J Rettig & M D Gorrell 1999 Fibroblast activation protein: A cell surface dipeptidyl peptidase and gelatinase expressed by stellate cells at the tissue remodelling interface in human cirrhosis *Hepavology* 29: 1768–78.
10. De Meester I, S Korom, J Van Damme & S Scharpé1999 CD26, let it cut or cut it down *Immunology Today* 20: 367–75.
11. Natural substrates of dipeptidyl peptidase IV. De Meester I, C Durinx, G Bal, P Proost, S Struyf, F Goossens, K Augustyns & S Scharpé. 2000, in *Cellular Peptidases in Immune Functions and Diseases II*, J Langner & S Ansorge, Editor. Kluwer: New York. p. 67—88.
12. Mentlein R 1999 Dipeptidyl-peptidase IV (CD26): role in the inactivation of regulatory peptides *Regulatory Peptides* 85: 9–24.
13. Morrison M E, S Vijayasaradhi, D Engelstein, A P Albino & A N Houghton 1993 A marker for neoplastic progression of human melanocytes is a cell surface ectopeptidase *Journal of Experimental Medicine* 177: 1135–43.
14. Mueller S C, G Ghersi, S K Akiyama, Q X A Sang, L Howard, M Pineiro-Sanchez, H Nakahara, Y Yeh & WT Chen 1999 A novel protease-docking function of integrin at invadopodia *Journal of Biological Chemistry* 274: 24947–52.
15. Holst J J & C F Deacon 1998 Inhibition of the activity of dipeptidyl-peptidase IV as a treatment for type 2 diabetes *Diabetes* 47: 1663–70.
16. Marguet D, L Baggio, T Kobayashi, AM Bernard, M Pierres, P F Nielsen, U Ribel, T Watanabe, D J Drucker & N Wagtmann 2000 Enhanced insulin secretion and improved glucose tolerance in mice lacking CD26 Proceedings of the *National Academy of Sciences of the United States of America* 97: 6874–9.
17. Ohtsuki T, H Tsuda & C Morimoto 2000 Good or evil: CD26 and HIV infection *Journal of Dermatological Science* 22: 152–60.
18. Wesley U V, A P Albino, S Tiwari & A N Houghton 1999 A role for dipeptidyl peptidase IV in suppressing the malignant phenotype of melanocytic cells *Journal of Experimental Medicine* 190: 311–22.
19. Korom S, I De Meester, T H W Stadlbauer, A Chandraker, M Schaub, M H Sayegh, A Belyaev, A Haemers, S Scharpé & J W Kupiecweglinski 1997 Inhibition of CD26/dipeptidyl peptidase IV activity in vivo prolongs cardiac allograft survival in rat recipients *Transplantation* 63: 1495–500.
20. Tanaka S, T Murakami, H Horikawa, M Sugiura, K Kawashima & T Sugita 1997 Suppression of arthritis by the inhibitors of dipeptidyl peptidase IV International *Journal of Immunopharmacology* 19: 15–24.
21. Augustyns K, G Bal, G Thonus, A Belyaev, X M Zhang, W Bollaert, A M Lambeir, C Durinx, F Goossens & A Haemers 1999 The unique properties of dipeptidyl-peptidase IV (DPP IV/CD26) and the therapeutic potential of DPP IV inhibitors *Current Medicinal Chemistry* 6: 311–27.
22. Hinke SA, JA Pospisilik, HU Demuth, S Mannhart, K Kuhn-Wache, T Hoffmannn, E Nishimura, R A Pederson & C H S McIntosh 2000 Dipeptidyl peptidase IV (DPIV/CD26) degradation of glucagon—Characterization of glucagon degradation products and DPIV-resistant analogs *Journal of Biological Chemistry* 275: 3827–34.
23. Korom S, I De Meester, A Coito, E Graser, H D Volk, K Schwemmle, S Scharpe & J W Kupiec-Weglinski 1999 Immunomodulatory influence of CD26 dipeptidylpeptidase IV during acute and accelerated rejection *Langenbecks Archives of Surgery* 1: 241–5.
24. Tavares W, D J Drucker & P L Brubaker 2000 Enzymatic- and renal-dependent catabolism of the intestinotropic hormone glucagon-like peptide-2 in rats *American Journal of Physiology Endocrinology and Metabolism* 278: E134-E9.
25. David F, A M Bernard, M Pierres & D Marguet 1993 Identification of serine 624, aspartic acid 702, and histidine 734 as the catalytic triad residues of mouse dipeptidyl-peptidase IV (CD26). A member of a novel family of nonclassical serine hydrolases *J Biol Chem* 268: 17247–52.
26. Ogata S, Y Misumi, E Tsuji, N Takami, K Oda & Y Ikehara 1992 Identification of the active site residues in dipeptidyl peptidase IV by affinity labeling and site-directed mutagenesis Biochemistry 31: 2582–7.
27. Dipeptidyl peptidase IV (DPPIV/CD26): biochemistry and control of cell-surface expression. Trugnan G, T Ait-Slimane, F David, L Baricault, T Berbar, C Lenoir & C Sapin. 1997, in *Cell-Surface Peptidases in Health and Disease*, A J Kenny & C M Boustead, Editor. BIOS Scientific Publishers: Oxford. p. 203–17.
28. Steeg C, U Hartwig & B Fleischer 1995 Unchanged signaling capacity of mutant CD26/dipeptidylpeptidase IV molecules devoid of enzymatic activity *Cell Immunol* 164: 311–5.
29. Fulop V, Z Bocskei & L Polgar 1998 Prolyl oligopeptidase—an unusual beta-propeller domain regulates proteolysis *Cell* 94: 161–70.
30. Ausubel F M, R Brent, R E Kingston, D D Moore, J G Seidman, J A Smith & K Struhl, ed. Current Protocols in Molecular Biology. 1998, John Wiley & Sons: USA.
31. Molecular cloning: a laboratory manual. Sambrook J, E F Fritsch & T Maniatis. 1989. 2nd ed., Cold Spring Harbor: Cold Spring Harbor Laboratory Press.
32. Augustyns K J L, A M Lambeir, M Borloo, I Demeester, I Vedernikova, G Vanhoof, D Hendriks, S Scharpe & A Haemers 1997 Pyrrolidides—synthesis and structure-activity relationship as inhibitors of dipeptidyl peptidase IV *European Journal of Medicinal Chemistry* 32:301–9.
33. Stockel-Maschek A, C Mrestani-Klaus, B Stiebitz, H U Demuth & K Neubert 2000 Thioxo amino acid pyrrolidides and thiazolidides: new inhibitors of proline specific peptidases Biochimica et Biophysica Acta—*Protein Structure & Molecular Enzymology* 1479: 15–31.
34. Schon E, I Born, H U Demuth, J Faust, K Neubert, T Steinmetzer, A Barth & S Ansorge 1991 Dipeptidyl peptidase IV in the immune system. Effects of specific enzyme inhibitors on activity of dipeptidyl peptidase IV and proliferation of human lymphocytes *Biological Chemistry Hoppe Seyler* 372: 305–11.
35. Coligan J E, A M Kruisbeek, D H Margulies, E M Shevach & W Strober, eds. Current Protocols in Immunology. 1998, John Wiley & Sons: USA.
36. Fibroblast activation protein. Rettig W J. 1998, in *Handbook of Proteolytic Enzymes*, A J Barrett, N D Rawlings & J F Woessner, Editor. Academic Press: San Diego. p. 387–9.
37. McCaughan, G. W., Siah, C. L., Abbott, C., Wickson, J., Ballesteros, M. & Bishop, G. A. (1993) Dipeptidyl peptidase IV is down-regulated in rat hepatoma cells at the mRNA level, *J. Gastroenterol. Hepatol.* 8, 142–5.
38. Altschul, S. F., Gish, W., Miller, W., Myers, E. W. & Lipman, D. J. (1990) Basic local alignment search tool, *J. Mol. Diol.* 215, 403–410.
33. Callen, D. F., Baker, E., Eyre, H. J., Chernos, J. E., Bell, J. A. & Sutherland, G. R. (1990) Reassessment of two apparent deletions of chromosome 16p to an ins (11;16) and a t(1;16) by chromosome painting, *Annales De Genetique.* 33, 219–21.
39. Abbott, C. A., McCaughan, G. W., Levy, M. T., Church, W. B. & Gorrell, M. D. (1999) Binding to human dipeptidyl peptidase IV by adenosine deaminase and antibodies that inhibit ligand binding involves overlapping, discontinuous sites on a predicted beta propeller domain, *Eur. J. Biochem.* 266, 798–810.
40. McCaughan, G. W., Wickson, J. E., Creswick, P. F. & Gorrell, M. D. (1990) Identification of the bile canalicular cell surface molecule GP110 as the ectopeptidase dipeptidyl peptidase IV: an analysis by tissue distribution, purification and N-terminal amino acid sequence, *Hepatology.* 11, 534–44.
41. Gorrell, M. D., Wickson, J. & McCaughan, G. W. (1991) Expression of the rat CD26 antigen (dipeptidyl peptidase IV) on subpopulations of rat lymphocytes, *Cell. Immunol.* 134, 205–215.
42. Bishop, G. A., Rokahr, K. L., Napoli, J. & McCaughan, G. W. (1993) Intragraft cytokine mRNA levels in human liver allograft rejection analysed by reverse transcription and semiquantitative polymerase chain reaction amplification, *Transplant Immunol.* 1, 253–61.
43. Yoshimoto, T., Fischl, M., Orlowski, R. C. & Walter, R. (1978) Post-proline cleaving enzyme and post-proline dipeptidylpeptidase, *J. Biol. Chem.* 253, 3708–3716.
44. Fukasawa, K. M., Fukasawa, K., Hiraoka, B. Y. & Harada, M. (1981) Comparison of dipeptidyl peptidase IV prepared from pig liver and kidney, *Biochim. Biophys. Acta.* 657, 179–89.
45. Banbula, A., Mak, P., Bugno, M., Silberring, J., Dubin, A., Nelson, D., Travis, J. & Potempa, J. (1999) Prolyl tripeptidyl peptidase from Porphyromonas gingivalis. A novel enzyme with possible pathological implications for the development of periodontitis, *J. Biol. Chem.* 274, 9246–9252.
46. Wolf, G. B., Scherberich, J. E., Fischer, P. & Schoeppe, W. (1989) Isolation and characterization of dipeptidyl aminopeptidase IV from human kidney cortex, *Clin. Chim. Acta.* 179, 61–71.
47. Fox, D. A., Hussey, R. E., Fitzgerald, K. A., Acuto, O., Poole, C., Palley, L., Daley, J. F., Schlossman, S. F. & Reinherz, E. L. (1984) Tal, a novel 105 KD human T cell activation antigen defined by a monoclonal antibody, *J. Immunol.* 133, 1250–6.
48. Bühling, F., Kunz, D., Reinhold, D., Ulmer, A. J., Ernst, M., Flad, H. D. & Ansorge, S. (1994) Expression and functional role of dipeptidyl peptidase IV (CD26) on human natural killer cells, *Natural Immunity.* 13, 270–9.
49. Buhling, F., Junker, U., Reinhold, D., Neubert, K., Jager, L. & Ansorge, S. (1995) Functional role of CD26 on human B lymphocytes, *Immunol Lett.* 45, 47–51.
50. Flentke, G. R., Munoz, E., Huber, B. T., Plaut, A. G., Kettner, C. A. & Bachovchin, W. W. (1991) Inhibition of dipeptidyl aminopeptidase IV (DP-IV) by Xaa-boroPro dipeptides and use of these inhibitors to examine the role of DP-IV in T-cell function, *Proc. Natl. Acad. Sci. USA.* 88, 1556–9.
51. Schön, E., Jahn, S., Kiessig, S. T., Demuth, H. U., Neubert, K., Barth, A., Von-Bahr, R. & Ansorge, S. (1987) The role of dipeptidyl peptidase Iv in human T lymphocyte activation. Inhibitors and antibodies against dipeptidyl peptidase IV suppress lymphocyte proliferation and immunoglobulin synthesis in vitro, *Eur. J. Immunol.* 17, 1821–6.
52. Schön, E., Born, I., Demuth, H. U., Faust, J., Neubert, K., Steinmetzer, T., Barth, A. & Ansorge, S. (1991) Dipeptidyl peptidase IV in the immune system. Effects of specific enzyme inhibitors on activity of dipeptidyl peptidase IV and proliferation of human lymphocytes, *Biol. Chem. Hoppe Seyler.* 372, 305–11.
53. Reinhold, D., Hemmer, B., Gran, B., Born, I., Faust, J., Neubert, K., McFarland, H. F., Martin, R. & S Ansorge, S. (1998) Inhibitors of dipeptidyl peptidase IV/CD26 suppress activation of human MBP-specific CD4+T cell clones, *J. Neuroimmunol.* 87, 203–9.
54. Kähne, T., Neubert, K., Faust, J. & Ansorge, S. (1998) Early phosphorylation events induced by DPIV/CD26-specific inhibitors, Cell. Immunol. 189, 60–66.
55. Korom, S., De Meester, I., Stadlbauer, T. H. W., Chandraker, A., Schaub, M., Sayegh, M. H., Belyaev, A., Haemers, A., Scharpé, S. & Kupiecweglinski, J. W. (1997) Inhibition of CD26/dipeptidyl peptidase IV activity in vivo prolongs cardiac allograft survival in rat recipients, *Transplantation.* 63, 1495–1500.
56. Bednarczyk, J. L., Carroll, S. M., Marin, C. & McIntyre, B. W. (1991) Triggering of the proteinase dipeptidyl peptidase IV (CD26) amplifies human T lymphocyte proliferation, *J. Cell. Biochem.* 46, 206–18.
57. De Meester, I., Vanhoof, C., Hendriks, D., Demuth, H. U., Yaron, A. & Scharpé,S. (1992) Characterization of dipeptidyl peptidase IV (CD26) from human lymphocytes, *Clin. Chim. Acta.* 210, 23–34.
58. Goossens, F., De Meester, I., Vanhoof, G., Hendriks, D., Vriend, G. & Scharpe, S. (1995) The purification, characterization and analysis of primary and secondary-structure of prolyl oligopeptidase from human lymphocytes. Evidence that the enzyme belongs to the alpha/beta hydrolase fold family, *Eur. J. Biochem.* 233, 432–441.
59. Walter, R., Simmons, W. H. & Yoshimoto, T. (1980) Proline specific endo- and exopeptidases, *Mol. Cell. Bioc.* 30, 111–27.
60. Abbott, C. A., Baker, E., Sutherland, G. R. & McCaughan, G. W. (1994) Genomic organisation, exact localization, and tissue expression of the human CD26 (dipeptidyl peptidase IV) gene, *Immunogenetics.* 40, 331–338.

61. Mathew, S., Scanlan, M. J., Mohan Raj, B. K., Murty, V. V., Garin-Chesa, P., Old, L. J., Rettig, W. J. & Chaganti, R. S. (1995) The gene for fibroblast activation protein alpha (FAP), a putative cell surface-bound serine protease expressed in cancer stroma and wound healing, maps to chromosome band 2q23, *Genomics.* 25, 335–337.

62. Yokotani, N., Doi, K., Wenthold, R. J. & Wada, K. (1993) Non-conservation of a catalytic residue in a dipeptidyl aminopeptidase IV-related protein encoded by a gene on human chromosome 7, Hum. Mol. Genet. 2, 1037–9.

63. Goossens, F. J., Wauters, J. G., Vanhoof, G. C., Bossuyt, P. J., Schatteman, K. A., Loens, K. & Scharpé,S. (1996) Subregional mapping of the human lymphocyte prolyl oligopeptidase gene (PREP) to human chromosome 6q22, *Cytogenet Cell Genet.* 74, 99–101.

64. Campbell, D. A., McHale, D. P., Brown, K. A., Moynihan, L. M., Houseman, M., Karbani, G., Parry, G., Janjua, A. H., Newton, V., Al-Gazali, L., Markham, A. F., Lench, N. J. & Mueller, R. F. (1997) A new locus for non-syndromal autosomal recessive, sensorineural hearing loss (DFNB16) maps to human chromosome 15q21–q22, *J. Med. Genet.* 34, 1015–7.

65. Bruford, E. A., Riise, R., Teague, P. W., Porter, K., Thomson, K. L., Moore, A. T., Jay, M., Warburg, M., Schinzel, A., Tommerup, N., Tornqvist, K., Rosenberg, T., Patton,. M., Mansfield, D. C. & Wright, A. F. (1997) Linkage mapping in 29 Bardet-Biedl syndrome families confirms loci in chromosomal regions 11q13, 15q22.3–q23, and 16q21, Genomics. 41, 93–9.

66. Duke-Cohan, J. S., Gu, J., McLaughlin, D. F., Xu, Y., Freeman, G. J. & Schlossman, S. F. (1998) Attractin (DPPT-L), a member of the CUB family of cell adhesion and guidance proteins, is secreted by activated human T lymphocytes and modulates immune cell interactions, *Proc. Natl. Acad. Sci. USA.* 95, 11336–11341.

67. Gunn, T. M., Miller, K. A., He, L., Hyman, R. V., Davis, R. W., Azarani, A., Schlossman, S. F., Duke-Cohan, J. S. & Barsh, G. S. (1999) The mouse mahogany locus encodes a transmembrane form of human attractin, *Nature.* 398, 152–156.

68. Drucker, D. J., Shi, Q., Crivici, A., Sumnersmith, M., Tavares, W., Hill, M., Deforest, L., Cooper, S. & Brubaker, P. L. (1997) Regulation of the biological activity of glucagon-like peptide 2 in vivo by dipeptidyl peptidase IV, Nature Biotechnol. 15, 673–677.

69. Smith, R. E., Reynolds, C. J. & Elder, E. A. (1992) The evolution of proteinase substrates with special reference to dipeptidylpeptidase IV, *Histochem. J.* 24, 637–47.

70. Blanco, J., Nguyen, C., Callebaut, C., Jacotot, E., Krust, B., Mazaleyrat, J. P., Wakselman, M. & Hovanessian, A. G. (1998) Dipeptidyl-peptidase IV-beta. Further characterization and comparison to dipeptidyl-peptidase IV activity of CD26, *Eur. J. Biochem.* 256, 369–78.

71. Niedermeyer, J., Scanlan, M. J., Garin-Chesa, P., Daiber, C., Fiebig, H. H., Old, L. J., Rettig, W. J. & Schnapp, A. (1997) Mouse fibroblast activation protein: molecular cloning, alternative splicing and expression in the reactive stroma of epithelial cancers, *Int. J. Cancer.* 71, 383–9.

72. Goldstein, L. A. & Chen, W. T. (2000) Identification of an alternatively spliced seprase mRNA that encodes a novel intracellular isoform, *J. Biol. Chem.* 275, 2554–2559.

73. Hough, R. B., Lengeling, A., Bedian, V., Lo, C. & Bucan, M. (1998) Rump white inversion in the mouse disrupts dipeptidyl aminopeptidase-like protein 6 and causes dysregulation of Kit expression, *Proc. Natl . Acad. Sci. USA.* 95, 13800–13805.

---

What is claimed is:

1. An isolated peptide which comprises:
   (a) the sequence shown in SEQ ID NO:1; or
   (b) a sequence which has at least 95% identity with the sequence shown in SEQ ID NO:1, and which has the same substrate specificity as SEQ ID NO:1.

2. A fragment of the sequence shown in SEQ ID NO:1 which has the same substrate specificity as SFQ ID NO: 1.

3. A fragment according to claim 2 which consisis of the sequence shown in SEQ ID NO.s: 3, 5 or 7.

4. A peptide according to claim 1, wherein an asparaginc residue in the peptide is not linked to a carbohydrate molecule.

5. A peptide according to claim 1, wherein the peptide is not expressed on the cell surface membrane of a cell.

6. A fusion protein comprising the amino acid sequence shown in SEQ ID NO:1 linked with a further amino acid sequence, the fusion protein having the same substrate specificity as SEQ ID NO:1.

7. A fusion protein according to claim 6 wherein the further amino acid sequence is selected from the group consisting of GST, V5 epitope and His tag.

8. A composition comprising a peptide according to claim 1.

* * * * *

UNITED STATES PATENT AND TRADEMARK OFFICE
CERTIFICATE OF CORRECTION

PATENT NO. : 6,881,564 B1
DATED : April 19, 2005
INVENTOR(S) : Catherine Anne Abbott et al.

It is certified that error appears in the above-identified patent and that said Letters Patent is hereby corrected as shown below:

Column 1,
Line 25, "activity[8,9]" should be -- activity [8,9] --.
Line 48, "[9,20]" should be -- [19,20] --.

Column 2,
Line 33, "AspGluAsnValllisPheAlaHis" should be -- AspGluAsnValHisPheAlaHis --.
Line 34, "ArgHisSerlleArg" should be -- ArgHisSerIleArg --.
Line 38, "nmultiple" should be -- multiple --.
Line 58, "ValleuGlnGluGluPhe (SEQ ID NO i6)" should be -- ValLeuGlnGluGluPhe (SEQ ID NO: 16) --.

Column 3,
Line 5, before "sequence" insert -- of the --.

Column 8,
Line 59, "GenBankwm[TM]" should be -- Genbank[TM] --.

Column 11,
Line 27, "Talons[®]" should be -- Talon[®] --.
Line 55, "for is min" should be -- for 15 min --.

Column 17,
Line 45, "[621]" should be -- [62] --.

Column 18,
Line 15, "transcript(9)" should be -- transcript(s) --.

Column 19,
Line 13, "*Hepavology*" should be -- *Hepatology* --.

Column 21,
Line 16, "*Diol.*" should be -- *Biol.* --.

Column 22,
Line 30, "Martin, R. & S" should be -- Martin, R. & --.

UNITED STATES PATENT AND TRADEMARK OFFICE
CERTIFICATE OF CORRECTION

PATENT NO. : 6,881,564 B1
DATED : April 19, 2005
INVENTOR(S) : Catherine Anne Abbott et al.

It is certified that error appears in the above-identified patent and that said Letters Patent is hereby corrected as shown below:

Column 45,
Line 47, after "has" insert -- dipeptidyl peptidase activity, with --.
Line 48, after "specificity" insert a comma -- , --.
Line 49, after "has" insert -- dipeptidyl peptidase activity, with --.
Line 49, after "specificity" insert a comma -- , --.
Line 49, "SFQ" should be -- SEQ --.
Line 51, after "claim 2" insert a comma -- , --.
Line 51, "consisis" should be -- consists --.
Line 52, "SEQ ID NO.s: 3, 5 or 7" should be -- SEQ ID NOs: 3 or 5 --.
Line 53, "asparaginc" should be -- asparagine --.

Column 46,
Line 47, after "having" insert -- dipeptidyl peptidase activity, with --.
Line 48, after "specificity" insert a comma -- , --.

Signed and Sealed this

Thirteenth Day of December, 2005

JON W. DUDAS
*Director of the United States Patent and Trademark Office*

SEQUENCE LISTING

<160> NUMBER OF SEQ ID NOS: 23

<210> SEQ ID NO 1
<211> LENGTH: 882
<212> TYPE: PRT
<213> ORGANISM: Homo Sapiens

<400> SEQUENCE: 1

```
Met Ala Ala Ala Met Glu Thr Glu Gln Leu Gly Val Glu Ile Phe Glu
1               5                   10                  15

Thr Ala Asp Cys Glu Glu Asn Ile Glu Ser Gln Asp Arg Pro Lys Leu
            20                  25                  30

Glu Pro Phe Tyr Val Glu Arg Tyr Ser Trp Ser Gln Leu Lys Lys Leu
        35                  40                  45

Leu Ala Asp Thr Arg Lys Tyr His Gly Tyr Met Met Ala Lys Ala Pro
    50                  55                  60

His Asp Phe Met Phe Val Lys Arg Asn Asp Pro Asp Gly Pro His Ser
65                  70                  75                  80

Asp Arg Ile Tyr Tyr Leu Ala Met Ser Gly Glu Asn Arg Glu Asn Thr
                85                  90                  95
```

```
Leu Phe Tyr Ser Glu Ile Pro Lys Thr Ile Asn Arg Ala Ala Val Leu
                100                 105                 110
Met Leu Ser Trp Lys Pro Leu Leu Asp Leu Phe Gln Ala Thr Leu Asp
            115                 120                 125
Tyr Gly Met Tyr Ser Arg Glu Glu Leu Leu Arg Glu Arg Lys Arg
        130                 135                 140
Ile Gly Thr Val Gly Ile Ala Ser Tyr Asp Tyr His Gln Gly Ser Gly
145                 150                 155                 160
Thr Phe Leu Phe Gln Ala Gly Ser Gly Ile Tyr His Val Lys Asp Gly
                165                 170                 175
Gly Pro Gln Gly Phe Thr Gln Pro Leu Arg Pro Asn Leu Val Glu
            180                 185                 190
Thr Ser Cys Pro Asn Ile Arg Met Asp Pro Lys Leu Cys Pro Ala Asp
                195                 200                 205
Pro Asp Trp Ile Ala Phe Ile His Ser Asn Asp Ile Trp Ile Ser Asn
        210                 215                 220
Ile Val Thr Arg Glu Glu Arg Leu Thr Tyr Val His Asn Glu Leu
225                 230                 235                 240
Ala Asn Met Glu Glu Asp Ala Arg Ser Ala Gly Val Ala Thr Phe Val
                245                 250                 255
Leu Gln Glu Glu Phe Asp Arg Tyr Ser Gly Tyr Trp Trp Cys Pro Lys
            260                 265                 270
Ala Glu Thr Thr Pro Ser Gly Gly Lys Ile Leu Arg Ile Leu Tyr Glu
        275                 280                 285
Glu Asn Asp Glu Ser Glu Val Glu Ile Ile His Val Thr Ser Pro Met
        290                 295                 300
Leu Glu Thr Arg Arg Ala Asp Ser Phe Arg Tyr Pro Lys Thr Gly Thr
305                 310                 315                 320
Ala Asn Pro Lys Val Thr Phe Lys Met Ser Glu Ile Met Ile Asp Ala
                325                 330                 335
Glu Gly Arg Ile Ile Asp Val Ile Asp Lys Glu Leu Ile Gln Pro Phe
            340                 345                 350
Glu Ile Leu Phe Glu Gly Val Glu Tyr Ile Ala Arg Ala Gly Trp Thr
        355                 360                 365
Pro Glu Gly Lys Tyr Ala Trp Ser Ile Leu Leu Asp Arg Ser Gln Thr
        370                 375                 380
Arg Leu Gln Ile Val Leu Ile Ser Pro Glu Leu Phe Ile Pro Val Glu
385                 390                 395                 400
Asp Asp Val Met Glu Arg Gln Arg Leu Ile Glu Ser Val Pro Asp Ser
                405                 410                 415
Val Thr Pro Leu Ile Ile Tyr Glu Glu Thr Thr Asp Ile Trp Ile Asn
            420                 425                 430
Ile His Asp Ile Phe His Val Phe Pro Gln Ser His Glu Glu Glu Ile
        435                 440                 445
Glu Phe Ile Phe Ala Ser Glu Cys Lys Thr Gly Phe Arg His Leu Tyr
        450                 455                 460
Lys Ile Thr Ser Ile Leu Lys Glu Ser Lys Tyr Lys Arg Ser Ser Gly
465                 470                 475                 480
Gly Leu Pro Ala Pro Ser Asp Phe Lys Cys Pro Ile Lys Glu Glu Ile
                485                 490                 495
Ala Ile Thr Ser Gly Glu Trp Glu Val Leu Gly Arg His Gly Ser Asn
            500                 505                 510
Ile Gln Val Asp Glu Val Arg Arg Leu Val Tyr Phe Glu Gly Thr Lys
```

```
                515                 520                 525
Asp Ser Pro Leu Glu His His Leu Tyr Val Val Ser Tyr Val Asn Pro
    530                 535                 540

Gly Glu Val Thr Arg Leu Thr Asp Arg Gly Tyr Ser His Ser Cys Cys
545                 550                 555                 560

Ile Ser Gln His Cys Asp Phe Phe Ile Ser Lys Tyr Ser Asn Gln Lys
                565                 570                 575

Asn Pro His Cys Val Ser Leu Tyr Lys Leu Ser Ser Pro Glu Asp Asp
            580                 585                 590

Pro Thr Cys Lys Thr Lys Glu Phe Trp Ala Thr Ile Leu Asp Ser Ala
        595                 600                 605

Gly Pro Leu Pro Asp Tyr Thr Pro Pro Glu Ile Phe Ser Phe Glu Ser
    610                 615                 620

Thr Thr Gly Phe Thr Leu Tyr Gly Met Leu Tyr Lys Pro His Asp Leu
625                 630                 635                 640

Gln Pro Gly Lys Lys Tyr Pro Thr Val Leu Phe Ile Tyr Gly Gly Pro
                645                 650                 655

Gln Val Gln Leu Val Asn Asn Arg Phe Lys Gly Val Lys Tyr Phe Arg
            660                 665                 670

Leu Asn Thr Leu Ala Ser Leu Gly Tyr Val Val Val Ile Asp Asn
        675                 680                 685

Arg Gly Ser Cys His Arg Gly Leu Lys Phe Glu Gly Ala Phe Lys Tyr
    690                 695                 700

Lys Met Gly Gln Ile Glu Ile Asp Asp Gln Val Glu Gly Leu Gln Tyr
705                 710                 715                 720

Leu Ala Ser Arg Tyr Asp Phe Ile Asp Leu Asp Arg Val Gly Ile His
                725                 730                 735

Gly Trp Ser Tyr Gly Gly Tyr Leu Ser Leu Met Ala Leu Met Gln Arg
            740                 745                 750

Ser Asp Ile Phe Arg Val Ala Ile Ala Gly Ala Pro Val Thr Leu Trp
        755                 760                 765

Ile Phe Tyr Asp Thr Gly Tyr Thr Glu Arg Tyr Met Gly His Pro Asp
    770                 775                 780

Gln Asn Glu Gln Gly Tyr Tyr Leu Gly Ser Val Ala Met Gln Ala Glu
785                 790                 795                 800

Lys Phe Pro Ser Glu Pro Asn Arg Leu Leu Leu Leu His Gly Phe Leu
                805                 810                 815

Asp Glu Asn Val His Phe Ala His Thr Ser Ile Leu Leu Ser Phe Leu
            820                 825                 830

Val Arg Ala Gly Lys Pro Tyr Asp Leu Gln Ile Tyr Pro Gln Glu Arg
        835                 840                 845

His Ser Ile Arg Val Pro Glu Ser Gly Glu His Tyr Glu Leu His Leu
    850                 855                 860

Leu His Tyr Leu Gln Glu Asn Leu Gly Ser Arg Ile Ala Ala Leu Lys
865                 870                 875                 880

Val Ile

<210> SEQ ID NO 2
<211> LENGTH: 3120
<212> TYPE: DNA
<213> ORGANISM: Homo Sapiens

<400> SEQUENCE: 2
aagtgctaaa gcctccgagg ccaaggccgc tgctactgcc gccgctgctt cttagtgccg      60
```

-continued

```
cgttcgccgc ctgggttgtc accggcgccg ccgccgagga agccactgca accaggaccg      120
gagtggaggc ggcgcagcat gaagcggcgc aggcccgctc catagcgcac gtcgggacgg      180
tccgggcggg gccgggggga aggaaaatgc aacatggcag cagcaatgga aacagaacag      240
ctgggtgttg agatatttga aactgcggac tgtgaggaga atattgaatc acaggatcgg      300
cctaaattgg agccttttta tgttgagcgg tattcctgga gtcagcttaa aaagctgctt      360
gccgatacca gaaaatatca tggctacatg atggctaagg caccacatga tttcatgttt      420
gtgaagagga atgatccaga tggacctcat tcagacagaa tctattacct tgccatgtct      480
ggtgagaaca gagaaaatac actgttttat tctgaaattc ccaaaactat caatagagca      540
gcagtcttaa tgctctcttg gaagcctctt ttggatcttt ttcaggcaac actggactat      600
ggaatgtatt ctcgagaaga agaactatta agagaaagaa aacgcattgg aacagtcgga      660
attgcttctt acgattatca ccaaggaagt ggaacatttc tgtttcaagc cggtagtgga      720
atttatcacg taaagatgg agggccacaa ggatttacgc aacaaccttt aaggcccaat      780
ctagtggaaa ctagttgtcc caacatacg atggatccaa aattatgccc cgctgatcca      840
gactggattg ctttatacac tagcaacgat atttggatat ctaacatcgt aaccagagaa      900
gaaaggagac tcacttatgt gcacaatgag ctagccaaca tggaagaaga tgccagatca      960
gctggagtcg ctacctttgt tctccaagaa gaatttgata gatattctgg ctattggtgg     1020
tgtccaaaag ctgaaacaac tcccagtggt ggtaaaattc ttagaattct atatgaagaa     1080
aatgatgaat ctgaggtgga aattattcat gttacatccc ctatgttgga aacaaggagg     1140
gcagattcat tccgttatcc taaaacaggt acagcaaatc ctaaagtcac ttttaagatg     1200
tcagaaataa tgattgatgc tgaaggaagg atcatagatg tcatagataa ggaactaatt     1260
caaccttttg agattctatt tgaaggagtt gaatatattg ccagagctgg atggactcct     1320
gagggaaaat atgcttggtc catcctacta gatcgctccc agactcgcct acagatagtg     1380
ttgatctcac ctgaattatt tatcccagta gaagatgatg ttatggaaag cagagactc     1440 attgagtcag tgcctgattc tgtgacgcca ctaattatct atgaagaaac aacagacatc     1500
tggataaata tccatgacat ctttcatgtt tttccccaaa gtcacgaaga ggaaattgag     1560 tttattttg cctctgaatg caaaacaggt ttccgtcatt tatacaaaat tacatctatt     1620
ttaaaggaaa gcaaatataa acgatccagt ggtgggctgc ctgctccaag tgatttcaag     1680
tgtcctatca agaggagat agcaattacc agtggtgaat gggaagttct tggccggcat     1740
ggatctaata tccaagttga tgaagtcaga aggctggtat attttgaagg caccaaagac     1800
tcccctttag agcatcacct gtacgtagtc agttacgtaa atcctggaga ggtgacaagg     1860
ctgactgacc gtggctactc acattcttgc tgcatcagtc agcactgtga cttctttata     1920
agtaagtata gtaaccagaa gaatccacac tgtgtgtccc tttacaagct atcaagtcct     1980
gaagatgacc caacttgcaa aacaaggaa ttttgggcca ccattttgga ttcagcaggt     2040
cctcttcctg actatactcc tccagaaatt ttctcttttg aaagtactac tggatttaca     2100
ttgtatggga tgctctacaa gcctcatgat ctacagcctg aaagaaata tcctactgtg     2160 ctgttcatat atggtggtcc tcaggtgcag ttggtgaata tcggtttaa aggagtcaag     2220 tatttccgct tgaatacccc tagcctctcta ggttatgtgg ttgtagtgat agacaacagg     2280
ggatcctgtc accagggct taaatttgaa ggcgccttta aatataaaat gggtcaaata     2340
gaaattgacg atcaggtgga aggactccaa tatctagctt ctcgatatga tttcattgac     2400
```

-continued

```
ttagatcgtg tgggcatcca cggctggtcc tatggaggat acctctccct gatggcatta    2460
atgcagaggt cagatatctt cagggttgct attgctgggg ccccagtcac tctgtggatc    2520
ttctatgata caggatacac ggaacgttat atgggtcacc ctgaccagaa tgaacagggc    2580
tattacttag gatctgtggc catgcaagca gaaaagttcc cctctgaacc aaatcgttta    2640
ctgctcttac atggtttcct ggatgagaat gtccattttg cacataccag tatattactg    2700
agttttttag tgagggctgg aaagccatat gatttacaga tctatcctca ggagagacac    2760
agcataagag ttcctgaatc gggagaacat tatgaactgc atcttttgca ctaccttcaa    2820
gaaaaccttg gatcacgtat tgctgctcta aaagtgatat aattttgacc tgtgtagaac    2880
tctctggtat acactggcta tttaaccaaa tgaggaggtt taatcaacag aaaacacaga    2940
attgatcatc acattttgat acctgccatg taacatctac tcctgaaaat aaatgtggtg    3000
ccatgcaggg gtctacggtt tgtggtagta atctaatacc ttaaccccac atgctcaaaa    3060
tcaaatgata catattcctg agagacccag caataccata agaattacta aaaaaaaaaa    3120
```

<210> SEQ ID NO 3
<211> LENGTH: 310
<212> TYPE: PRT
<213> ORGANISM: Homo Sapiens

<400> SEQUENCE: 3

```
Phe Glu Gly Thr Lys Asp Ser Pro Leu Glu His His Leu Tyr Val Val
 1               5                   10                  15

Ser Tyr Val Asn Pro Gly Glu Val Thr Arg Leu Thr Asp Arg Gly Tyr
             20                  25                  30

Ser His Ser Cys Cys Ile Ser Gln His Cys Asp Phe Phe Ile Ser Lys
         35                  40                  45

Tyr Ser Asn Gln Lys Asn Pro His Cys Val Ser Leu Tyr Lys Leu Ser
     50                  55                  60

Ser Pro Glu Asp Asp Pro Thr Cys Lys Thr Lys Glu Phe Trp Ala Thr
 65                  70                  75                  80

Ile Leu Asp Ser Ala Gly Pro Leu Pro Asp Tyr Thr Pro Pro Glu Ile
                 85                  90                  95

Phe Ser Phe Glu Ser Thr Thr Gly Phe Thr Leu Tyr Gly Met Leu Tyr
            100                 105                 110

Lys Pro His Asp Leu Gln Pro Gly Lys Lys Tyr Pro Thr Val Leu Phe
        115                 120                 125

Ile Tyr Gly Gly Pro Gln Gly Gln Ile Glu Ile Asp Asp Gln Val Glu
    130                 135                 140

Gly Leu Gln Tyr Leu Ala Ser Arg Tyr Asp Phe Ile Asp Leu Asp Arg
145                 150                 155                 160

Val Gly Ile His Gly Trp Ser Tyr Gly Gly Tyr Leu Ser Leu Met Ala
                165                 170                 175

Leu Met Gln Arg Ser Asp Ile Phe Arg Val Ala Ile Ala Gly Ala Pro
            180                 185                 190

Val Thr Leu Trp Ile Phe Tyr Asp Thr Gly Tyr Thr Glu Arg Tyr Met
        195                 200                 205

Gly His Pro Asp Gln Asn Glu Gln Gly Tyr Tyr Leu Gly Ser Val Ala
    210                 215                 220

Met Gln Ala Glu Lys Phe Pro Ser Glu Pro Asn Arg Leu Leu Leu Leu
225                 230                 235                 240

His Gly Phe Leu Asp Glu Asn Val His Phe Ala His Thr Ser Ile Leu
                245                 250                 255
```

```
Leu Ser Phe Leu Val Arg Ala Gly Lys Pro Tyr Asp Leu Gln Ile Tyr
            260                 265                 270

Pro Gln Glu Arg His Ser Ile Arg Val Pro Glu Ser Gly Glu His Tyr
        275                 280                 285

Glu Leu His Leu Leu His Tyr Leu Gln Glu Asn Leu Gly Ser Arg Ile
    290                 295                 300

Ala Ala Leu Lys Val Ile
305                 310

<210> SEQ ID NO 4
<211> LENGTH: 1197
<212> TYPE: DNA
<213> ORGANISM: Homo Sapiens

<400> SEQUENCE: 4
attttgaagg caccaaagac tccccttttag agcatcacct gtacgtagtc agttacgtaa      60
atcctggaga ggtgacaagg ctgactgacc gtggctactc acattcttgc tgcatcagtc     120
agcactgtga cttctttata agtaagtata gtaaccagaa gaatccacac tgtgtgtccc     180
tttacaagct atcaagtcct gaagatgacc caacttgcaa acaaaggaa ttttgggcca      240
ccattttgga ttcagcaggt cctcttcctg actatactcc tccagaaatt ttctcttttg     300
aaagtactac tggatttaca ttgtatggga tgctctacaa gcctcatgat ctacagcctg     360
gaaagaaata tcctactgtg ctgttcatat atggtggtcc tcagggtcaa atagaaattg     420
acgatcaggt ggaaggactc caatatctag cttctcgata tgatttcatt gacttagatc     480
gtgtgggcat ccacggctgg tcctatggag gatacctctc cctgatgcca ttaatgcaga     540
ggtcagatat cttcagggtt gctattgctg gggccccagt cactctgtgg atcttctatg     600
atacaggata cacggaacgt tatatgggtc accctgacca gaatgaacag ggctattact     660
taggatctgt ggccatgcaa gcagaaaagt tcccctctga accaaatcgt ttactgctct     720
tacatggttt cctggatgag aatgtccatt ttgcacatac cagtatatta ctgagttttt     780
tagtgagggc tggaaagcca tatgattac agatctatcc tcaggagaga cacagcataa     840
gagttcctga atcgggagaa cattatgaac tgcatctttt gcactacctt caagaaaacc     900
ttggatcacg tattgctgct ctaaaagtga taatttttg acctgtgtag aactctctgg     960
tatacactgg ctatttaacc aaatgaggag gtttaatcaa cagaaaacac agaattgatc    1020
atcacattttt gatacctgcc atgtaacatc tactcctgaa ataaatgtg gtgccatgca    1080
ggggtctacg gtttgtggta gtaatctaat accttaaccc cacatgctca aaatcaaatg    1140
atacatattc ctgagagacc cagcaatacc ataagaatta ctaaaaaaaa aaaaaaa        1197

<210> SEQ ID NO 5
<211> LENGTH: 465
<212> TYPE: PRT
<213> ORGANISM: Homo Sapiens

<400> SEQUENCE: 5

Thr Gly Thr Ala Asn Pro Lys Val Thr Phe Lys Met Ser Glu Ile Met
  1               5                  10                  15

Ile Asp Ala Glu Gly Arg Ile Ile Asp Val Ile Asp Lys Glu Leu Ile
                20                  25                  30

Gln Pro Phe Glu Ile Leu Phe Glu Gly Val Glu Tyr Ile Ala Arg Ala
            35                  40                  45

Gly Trp Thr Pro Glu Gly Lys Tyr Ala Trp Ser Ile Leu Leu Asp Arg
```

```
                 50                   55                  60
Ser Gln Thr Arg Leu Gln Ile Val Leu Ile Ser Pro Glu Leu Phe Ile
 65                      70                  75                  80

Pro Val Glu Asp Asp Val Met Glu Arg Gln Arg Leu Ile Glu Ser Val
                 85                  90                  95

Pro Asp Ser Val Thr Pro Leu Ile Ile Tyr Glu Glu Thr Thr Asp Ile
                100                 105                 110

Trp Ile Asn Ile His Asp Ile Phe His Val Phe Pro Gln Ser His Glu
                115                 120                 125

Glu Glu Ile Glu Phe Ile Phe Ala Ser Glu Cys Lys Thr Gly Phe Arg
130                     135                 140

His Leu Tyr Lys Ile Thr Ser Ile Leu Lys Glu Ser Lys Tyr Lys Arg
145                 150                 155                 160

Ser Ser Gly Gly Leu Pro Ala Pro Ser Asp Phe Lys Cys Pro Ile Lys
                165                 170                 175

Glu Glu Ile Ala Ile Thr Ser Gly Glu Trp Glu Val Leu Gly Arg His
                180                 185                 190

Gly Ser Asn Ile Gln Val Asp Glu Val Arg Arg Leu Val Tyr Phe Glu
                195                 200                 205

Gly Thr Lys Asp Ser Pro Leu Glu His His Leu Tyr Val Val Ser Tyr
210                     215                 220

Val Asn Pro Gly Glu Val Thr Arg Leu Thr Asp Arg Gly Tyr Ser His
225                     230                 235                 240

Ser Cys Cys Ile Ser Gln His Cys Asp Phe Phe Ile Ser Lys Tyr Ser
                245                 250                 255

Asn Gln Lys Asn Pro His Cys Val Ser Leu Tyr Lys Leu Ser Ser Pro
                260                 265                 270

Glu Asp Asp Pro Thr Cys Lys Thr Lys Glu Phe Trp Ala Thr Ile Leu
                275                 280                 285

Asp Ser Ala Gly Pro Leu Pro Asp Tyr Thr Pro Pro Glu Ile Phe Ser
                290                 295                 300

Phe Glu Ser Thr Thr Gly Phe Thr Leu Tyr Gly Met Leu Tyr Lys Pro
305                     310                 315                 320

His Asp Leu Gln Pro Gly Lys Lys Tyr Pro Thr Val Leu Phe Ile Tyr
                325                 330                 335

Gly Gly Pro Gln Val Ala Ile Ala Gly Ala Pro Val Thr Leu Trp Ile
                340                 345                 350

Phe Tyr Asp Thr Gly Tyr Thr Glu Arg Tyr Met Gly His Pro Asp Gln
                355                 360                 365

Asn Glu Gln Gly Tyr Tyr Leu Gly Ser Val Ala Met Gln Ala Glu Lys
                370                 375                 380

Phe Pro Ser Glu Pro Asn Arg Leu Leu Leu His Gly Phe Leu Asp
385                     390                 395                 400

Glu Asn Val His Phe Ala His Thr Ser Ile Leu Ser Phe Leu Val
                405                 410                 415

Arg Ala Gly Lys Pro Tyr Asp Leu Gln Ile Tyr Pro Gln Glu Arg His
                420                 425                 430

Ser Ile Arg Val Pro Glu Ser Gly Glu His Tyr Glu Leu His Leu Leu
                435                 440                 445

His Tyr Leu Gln Glu Asn Leu Gly Ser Arg Ile Ala Ala Leu Lys Val
                450                 455                 460

Ile
465
```

<210> SEQ ID NO 6
<211> LENGTH: 1669
<212> TYPE: DNA
<213> ORGANISM: Homo Sapiens

<400> SEQUENCE: 6

| | | | | | |
|---|---|---|---|---|---|
| aacaggtaca | gcaaatccta | aagtcacttt | taagatgtca | gaaataatga | ttgatgctga | 60 |
| aggaaggatc | atagatgtca | tagataagga | actaattcaa | ccttttgaga | ttctatttga | 120 |
| aggagttgaa | tatattgcca | gagctggatg | gactcctgag | ggaaaatatg | cttggtccat | 180 |
| cctactagat | cgctcccaga | ctcgcctaca | gatagtgttg | atctcacctg | aattatttat | 240 |
| cccagtagaa | gatgatgtta | tggaaaggca | gagactcatt | gagtcagtgc | ctgattctgt | 300 |
| gacgccacta | attatctatg | aagaaacaac | agacatctgg | ataaatatcc | atgacatctt | 360 |
| tcatgttttt | ccccaaagtc | acgaagagga | aattgagttt | attttttgcct | ctgaatgcaa | 420 |
| aacaggtttc | cgtcatttat | acaaaattac | atctatttta | aaggaaagca | aatataaacg | 480 |
| atccagtggt | gggctgcctg | ctccaagtga | tttcaagtgt | cctatcaaag | aggagatagc | 540 |
| aattaccagt | ggtgaatggg | aagttcttgg | ccggcatgga | tctaatatcc | aagttgatga | 600 |
| agtcagaagg | ctggtatatt | ttgaaggcac | caaagactcc | ccttagagc | atcacctgta | 660 |
| cgtagtcagt | tacgtaaatc | ctggagaggt | gacaaggctg | actgaccgtg | gctactcaca | 720 |
| ttcttgctgc | atcagtcagc | actgtgactt | ctttataagt | aagtatagta | accagaagaa | 780 |
| tccacactgt | gtgtcccttt | acaagctatc | aagtcctgaa | gatgacccaa | cttgcaaaac | 840 |
| aaaggaattt | tgggccacca | ttttggattc | agcaggtcct | cttcctgact | atactcctcc | 900 |
| agaaattttc | tcttttgaaa | gtactactgg | atttacattg | tatgggatgc | tctacaagcc | 960 |
| tcatgatcta | cagcctggaa | agaaatatcc | tactgtgctg | ttcatatatg | gtggtcctca | 1020 |
| ggttgctatt | gctggggccc | cagtcactct | gtggatcttc | tatgatacag | gatacacgga | 1080 |
| acgttatatg | ggtcaccctg | accagaatga | acagggctat | tacttaggat | ctgtggccat | 1140 |
| gcaagcagaa | aagttcccct | ctgaaccaaa | tcgtttactg | ctcttacatg | gtttcctgga | 1200 |
| tgagaatgtc | cattttgcac | ataccagtat | attactgagt | ttttagtga | gggctggaaa | 1260 |
| gccatatgat | ttacagatct | atcctcagga | gagacacagc | ataagagttc | ctgaatcggg | 1320 |
| agaacattat | gaactgcatc | ttttgcacta | ccttcaagaa | aaccttggat | cacgtattgc | 1380 |
| tgctctaaaa | gtgatataat | tttgaccctgt | gtagaactct | ctggtataca | ctggctattt | 1440 |
| aaccaaatga | ggaggtttaa | tcaacagaaa | acacagaatt | gatcatcaca | ttttgatacc | 1500 |
| tgccatgtaa | catctactcc | tgaaaataaa | tgtggtgcca | tgcagggggtc | tacggtttgt | 1560 |
| ggtagtaatc | taatacctta | accccacatg | ctcaaaatca | aatgatacat | attcctgaga | 1620 |
| gacccagcaa | taccataaga | attactaaaa | aaaaaaaaa | aaaaaaaaa | | 1669 |

<210> SEQ ID NO 7
<211> LENGTH: 360
<212> TYPE: PRT
<213> ORGANISM: Homo Sapiens

<400> SEQUENCE: 7

Glu Glu Asp Ala Arg Ser Ala Gly Val Ala Thr Phe Val Leu Gln Glu
 1               5                  10                  15

Glu Phe Asp Arg Tyr Ser Gly Tyr Trp Trp Cys Pro Lys Ala Glu   Thr
                20                  25                  30

| | | | | | | | | | | | | |
|---|---|---|---|---|---|---|---|---|---|---|---|---|
|Thr|Pro|Ser|Gly|Gly|Lys|Ile|Leu|Arg|Ile|Leu|Tyr|Glu|Glu|Asn|Asp|
| | |35| | | |40| | | |45| | |
|Glu|Ser|Glu|Val|Glu|Ile|Ile|His|Val|Thr|Ser|Pro|Met|Leu|Glu|Thr|
| |50| | | | |55| | | |60| | | |
|Arg|Arg|Ala|Asp|Ser|Phe|Arg|Tyr|Pro|Lys|Thr|Gly|Thr|Ala|Asn|Pro|
|65| | | | |70| | | |75| | | | |80|
|Lys|Val|Thr|Phe|Lys|Met|Ser|Glu|Ile|Met|Ile|Asp|Ala|Glu|Gly|Arg|
| | | | |85| | | |90| | | |95| |
|Ile|Ile|Val|Asp|Glu|Val|Arg|Arg|Leu|Val|Tyr|Phe|Glu|Gly|Thr|Lys|
| | | |100| | | |105| | | |110| | |
|Asp|Ser|Pro|Leu|Glu|His|His|Leu|Tyr|Val|Val|Ser|Tyr|Val|Asn|Pro|
| | |115| | | |120| | | |125| | |
|Gly|Glu|Val|Thr|Arg|Leu|Thr|Asp|Arg|Gly|Tyr|Ser|His|Ser|Cys|Cys|
| |130| | | | |135| | | |140| | | |
|Ile|Ser|Gln|His|Cys|Asp|Phe|Phe|Ile|Ser|Lys|Tyr|Ser|Asn|Gln|Lys|
|145| | | | |150| | | |155| | | | |160|
|Asn|Pro|His|Cys|Val|Ser|Leu|Tyr|Lys|Leu|Ser|Ser|Pro|Glu|Asp|Asp|
| | | |165| | | |170| | | |175| | |
|Pro|Thr|Cys|Lys|Thr|Lys|Glu|Phe|Trp|Ala|Thr|Ile|Leu|Asp|Ser|Ala|
| | |180| | | |185| | | |190| | |
|Gly|Pro|Leu|Pro|Asp|Tyr|Thr|Pro|Glu|Ile|Phe|Ser|Phe|Glu|Ser|
| |195| | | | |200| | | |205| | |
|Thr|Thr|Gly|Phe|Thr|Leu|Tyr|Gly|Met|Leu|Tyr|Lys|Pro|His|Asp|Leu|
| |210| | | | |215| | | |220| | | |
|Gln|Pro|Gly|Lys|Lys|Tyr|Pro|Thr|Val|Leu|Phe|Ile|Tyr|Gly|Gly|Pro|
|225| | | | |230| | | |235| | | | |240|
|Gln|Val|Gln|Leu|Val|Asn|Asn|Arg|Phe|Lys|Gly|Val|Lys|Tyr|Phe|Arg|
| | | |245| | | |250| | | |255| |
|Leu|Asn|Thr|Leu|Ala|Ser|Leu|Gly|Tyr|Val|Val|Val|Ile|Asp|Asn|
| | |260| | | | |265| | | |270| | |
|Arg|Gly|Ser|Cys|His|Arg|Gly|Leu|Lys|Phe|Glu|Gly|Ala|Phe|Lys|Tyr|
| |275| | | | |280| | | |285| | | |
|Lys|Met|Gly|Gln|Ile|Glu|Ile|Asp|Asp|Gln|Val|Glu|Gly|Leu|Gln|Tyr|
| |290| | | | |295| | | |300| | | |
|Leu|Ala|Ser|Arg|Tyr|Asp|Phe|Ile|Asp|Leu|Asp|Arg|Val|Gly|Ile|His|
|305| | | | |310| | | |315| | | | |320|
|Gly|Trp|Ser|Tyr|Gly|Gly|Tyr|Leu|Ser|Leu|Met|Ala|Leu|Met|Gln|Arg|
| | | |325| | | |330| | | |335| |
|Ser|Asp|Ile|Phe|Arg|Val|Ala|Ile|Ala|Gly|Ala|Pro|Val|Thr|Leu|Trp|
| | | |340| | | |345| | | |350| | |
|Ile|Phe|Tyr|Asp|Thr|Gly|Tyr|Thr|
| | | |355| | | |360|

<210> SEQ ID NO 8
<211> LENGTH: 1083
<212> TYPE: DNA
<213> ORGANISM: Homo Sapiens

<400> SEQUENCE: 8

```
ggaagaagat gccagatcag ctggagtcgc tacctttgtt ctccaagaag aatttgatag      60
atattctggc tattggtggt gtccaaaagc tgaaacaact cccagtggtg gtaaaattct     120
tagaattcta tatgaagaaa atgatgaatc tgaggtggaa attattcatg ttacatcccc     180
tatgttggaa acaaggaggg cagattcatt ccgttatcct aaaacaggta cagcaaatcc     240
```

```
taaagtcact tttaagatgt cagaaataat gattgatgct gaaggaagga tcatagttga     300
tgaagtcaga aggctggtat attttgaagg caccaaagac tcccctttag agcatcacct     360
gtacgtagtc agttacgtaa atcctggaga ggtgacaagg ctgactgacc gtggctactc     420
acattcttgc tgcatcagtc agcactgtga cttctttata agtaagtata gtaaccagaa     480
gaatccacac tgtgtgtccc tttacaagct atcaagtcct gaagatgacc caacttgcaa     540
aacaaaggaa ttttgggcca ccattttgga ttcagcaggt cctcttcctg actatactcc     600
tccagaaatt ttctcttttg aaagtactac tggattlaca ttgtatggga tgctctacaa     660
gcctcatgat ctacagcctg gaaagaaata tcctactgtg ctgttcatat atggtggtcc     720
tcaggtgcag ttggtgaata atcggtttaa aggagtcaag tatttccgct tgaatacccct    780 agcctctcta ggttatgtgg ttgtagtgat agacaacagg ggatcctgtc accgagggct    840
taaatttgaa ggcgccttta aatataaaat gggtcaaata gaaattgacg atcaggtgga    900
aggactccaa tatctagctt ctcgatatga tttcattgac ttagatcgtg tgggcatcca    960
cggctggtcc tatggaggat acctctccct gatggcatta atgcagaggt cagatatctt   1020
cagggttgct attgctgggg ccccagtcac tctgtggatc ttctatgata caggatacac   1080
gga                                                                 1083
```

<210> SEQ ID NO 9
<211> LENGTH: 9
<212> TYPE: PRT
<213> ORGANISM: Homo Sapiens

<400> SEQUENCE: 9

Tyr Gly Trp Ser Tyr Gly Gly Tyr Val
 1               5

<210> SEQ ID NO 10
<211> LENGTH: 7
<212> TYPE: PRT
<213> ORGANISM: Homo Sapiens

<400> SEQUENCE: 10

Ala Asp Asp Asn Val His Phe
 1               5

<210> SEQ ID NO 11
<211> LENGTH: 7
<212> TYPE: PRT
<213> ORGANISM: Homo Sapiens

<400> SEQUENCE: 11

Glu Asp His Gly Ile Ala Gln
 1               5

<210> SEQ ID NO 12
<211> LENGTH: 7
<212> TYPE: PRT
<213> ORGANISM: Homo Sapiens

<400> SEQUENCE: 12

Tyr Val Tyr Glu Glu Glu Val
 1               5

<210> SEQ ID NO 13
<211> LENGTH: 9
<212> TYPE: PRT
<213> ORGANISM: Homo Sapiens

```
<400> SEQUENCE: 13

His Gly Trp Ser Tyr Gly Gly Tyr Leu
1               5

<210> SEQ ID NO 14
<211> LENGTH: 8
<212> TYPE: PRT
<213> ORGANISM: Homo Sapiens

<400> SEQUENCE: 14

Leu Asp Glu Asn Val His Phe Ala
1               5

<210> SEQ ID NO 15
<211> LENGTH: 6
<212> TYPE: PRT
<213> ORGANISM: Homo Sapiens

<400> SEQUENCE: 15

Glu Arg His Ser Ile Arg
1               5

<210> SEQ ID NO 16
<211> LENGTH: 7
<212> TYPE: PRT
<213> ORGANISM: Homo Sapiens

<400> SEQUENCE: 16

Phe Val Leu Gln Glu Glu Phe
1               5

<210> SEQ ID NO 17
<211> LENGTH: 9
<212> TYPE: PRT
<213> ORGANISM: Homo Sapiens

<400> SEQUENCE: 17

Leu Asp Glu Asn Val His Phe Ala His
1               5

<210> SEQ ID NO 18
<211> LENGTH: 24
<212> TYPE: DNA
<213> ORGANISM: Artificial Sequence
<220> FEATURE:
<223> OTHER INFORMATION: PCR primers

<400> SEQUENCE: 18
ctgtgacgcc actaattatc tatg                                         24

<210> SEQ ID NO 19
<211> LENGTH: 24
<212> TYPE: DNA
<213> ORGANISM: Artificial Sequence
<220> FEATURE:
<223> OTHER INFORMATION: PCR primers

<400> SEQUENCE: 19
cctagagagg ctagggtatt caag                                         24

<210> SEQ ID NO 20
<211> LENGTH: 20
<212> TYPE: DNA
<213> ORGANISM: Artificial Sequence
```

```
<220> FEATURE:
<223> OTHER INFORMATION: PCR primers

<400> SEQUENCE: 20
accacagtcc atgccatcac                                               20

<210> SEQ ID NO 21
<211> LENGTH: 20
<212> TYPE: DNA
<213> ORGANISM: Artificial Sequence
<220> FEATURE:
<223> OTHER INFORMATION: PCR primers

<400> SEQUENCE: 21
tccaccaccc tgttgctgta                                               20

<210> SEQ ID NO 22
<211> LENGTH: 18
<212> TYPE: PRT
<213> ORGANISM: Artificial Sequence
<220> FEATURE:
<223> OTHER INFORMATION: Modified human peptide

<400> SEQUENCE: 22

Cys Thr Gly Tyr Thr Glu Arg Tyr Met Gly His Pro Asp Gln Asn Glu
 1               5                  10                  15

Gln Gly

<210> SEQ ID NO 23
<211> LENGTH: 16
<212> TYPE: PRT
<213> ORGANISM: Artificial Sequence
<220> FEATURE:
<223> OTHER INFORMATION: Modified peptide

<400> SEQUENCE: 23

Gly Lys Pro Tyr Asp Leu Gln Ile Tyr Pro Gln Glu Arg His Ser Cys
 1               5                  10                  15
```